(12) United States Patent
Kakimi et al.

(10) Patent No.: US 9,718,761 B2
(45) Date of Patent: Aug. 1, 2017

(54) METHOD FOR PRODUCING A-HYDROXYISOBUTYRIC ACID AMIDE AND REACTOR

(71) Applicant: MITSUBISHI GAS CHEMICAL COMPANY, INC., Tokyo (JP)

(72) Inventors: Atsushi Kakimi, Niigata (JP); Takako Uchiyama, Niigata (JP); Hideho Matsuda, Okayama (JP); Masaki Takemoto, Niigata (JP); Katsumi Higuchi, Tokyo (JP)

(73) Assignee: MITSUBISHI GAS CHEMICAL COMPANY, INC, Tokyo (JP)

( * ) Notice: Subject to any disclaimer, the term of this patent is extended or adjusted under 35 U.S.C. 154(b) by 9 days.

(21) Appl. No.: 14/903,375

(22) PCT Filed: Jul. 15, 2014

(86) PCT No.: PCT/JP2014/068755
§ 371 (c)(1),
(2) Date: Jan. 7, 2016

(87) PCT Pub. No.: WO2015/008740
PCT Pub. Date: Jan. 22, 2015

(65) Prior Publication Data
US 2016/0145196 A1  May 26, 2016

(30) Foreign Application Priority Data

Jul. 16, 2013  (JP) .................................. 2013-147932

(51) Int. Cl.
*C07C 231/06* (2006.01)
*B01J 23/34* (2006.01)
*B01J 19/00* (2006.01)

(52) U.S. Cl.
CPC ........... *C07C 231/065* (2013.01); *B01J 19/00* (2013.01); *B01J 23/34* (2013.01)

(58) Field of Classification Search
CPC ....... C07C 231/065; B01J 19/00; B01J 23/34; Y02P 20/52
(Continued)

(56) References Cited

U.S. PATENT DOCUMENTS 4,018,829 A  4/1977  Gruber et al.
4,950,801 A  8/1990  Ebata et al.
(Continued)

FOREIGN PATENT DOCUMENTS

CN  101987827  3/2011
EP  0 956 898  11/1999
(Continued)

OTHER PUBLICATIONS

International Search Report issued in Patent Application No. PCT/JP2014/068755, dated Sep. 16, 2014.
(Continued)

*Primary Examiner* — Jafar Parsa
*Assistant Examiner* — Amy C Bonaparte
(74) *Attorney, Agent, or Firm* — Greenblum & Bernstein, P.L.C.

(57) ABSTRACT

The present invention provides a method for producing α-hydroxyisobutyric acid amide by hydration of acetone cyanohydrin under the presence of a catalyst composed mainly of manganese oxide using a reactor in which at least two reaction regions are connected in series, the method being characterized by comprising: a step (B) of cyclically supplying at least a portion of a reaction liquid withdrawn from at least one reaction region to a first reaction region (I) in the reactor; and a step (b1) of further cyclically supplying at least a portion of the reaction liquid withdrawn from at
(Continued)

least one reaction region to at least one reaction region other than the first reaction region. The method is also characterized in that an oxidizing agent is supplied to at least one reaction region in the reactor.

11 Claims, 3 Drawing Sheets

(58) Field of Classification Search
IPC .................................................... Y02P 20/52
See application file for complete search history.

(56) References Cited

U.S. PATENT DOCUMENTS

| 4,987,256 | A | * | 1/1991 | Ebata | ................ | C07C 231/065 |
| | | | | | | 564/126 |
| 5,087,750 | A | | 2/1992 | Uda et al. | | |
| 5,463,123 | A | * | 10/1995 | Uchiyama | ........... | C07C 231/065 |
| | | | | | | 502/324 |
| 8,603,939 | B2 | * | 12/2013 | Uchiyama | .............. | B01J 23/002 |
| | | | | | | 502/324 |

| 2011/0004020 | A1 | 1/2011 | Shen et al. |
| 2011/0060159 | A1 | 3/2011 | May et al. |

FOREIGN PATENT DOCUMENTS

| JP | 52-222 | 1/1977 |
| JP | 2-196763 | 8/1990 |
| JP | 2-298718 | 12/1990 |
| JP | 3-188054 | 8/1991 |
| JP | 4-149164 | 5/1992 |
| JP | 6-172283 | 6/1994 |
| JP | 6-184072 | 7/1994 |
| JP | 7-76563 | 3/1995 |
| JP | 07-133256 | 5/1995 |
| JP | 2010-510276 | 4/2010 |

OTHER PUBLICATIONS

Wang et al., "A Study on the Characteristics of Hydrolysis and Esterification Reaction in the Production of Methyl Methacrylate (MMA)", Chemical Reaction Engineering and Technology; vol. 10, No. 3, Sep. 1994, pp. 217-226 with English Abstract thereof.

* cited by examiner

[Figure 1]
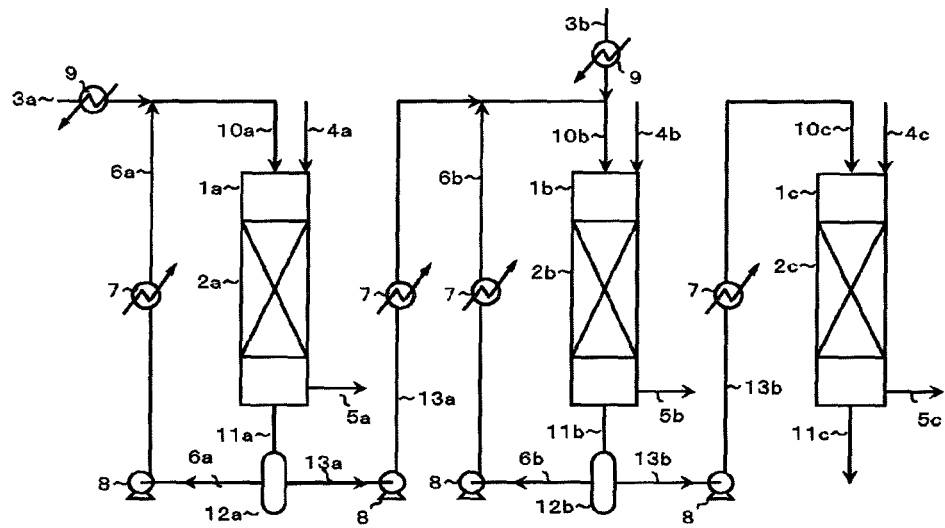
[Figure 2]
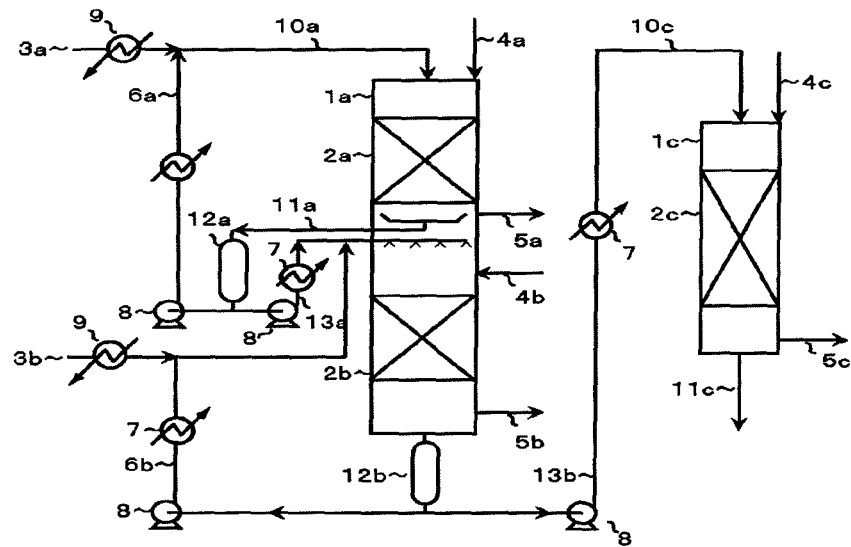

[Figure 3]
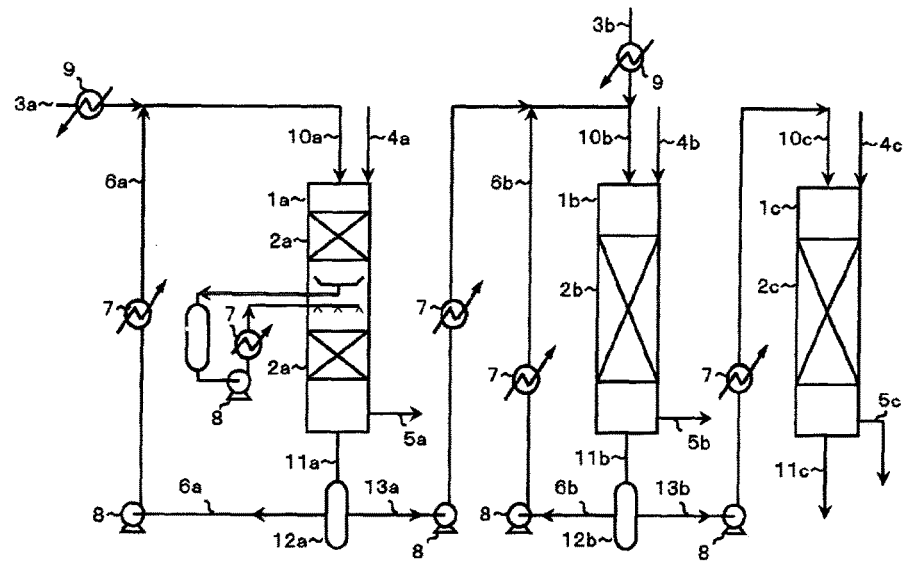
[Figure 4]
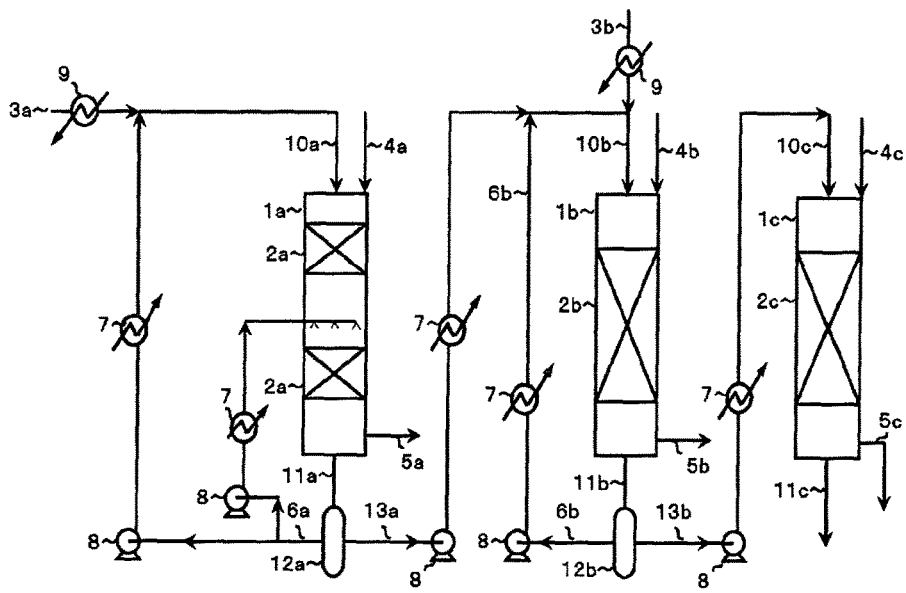

[Figure 5]
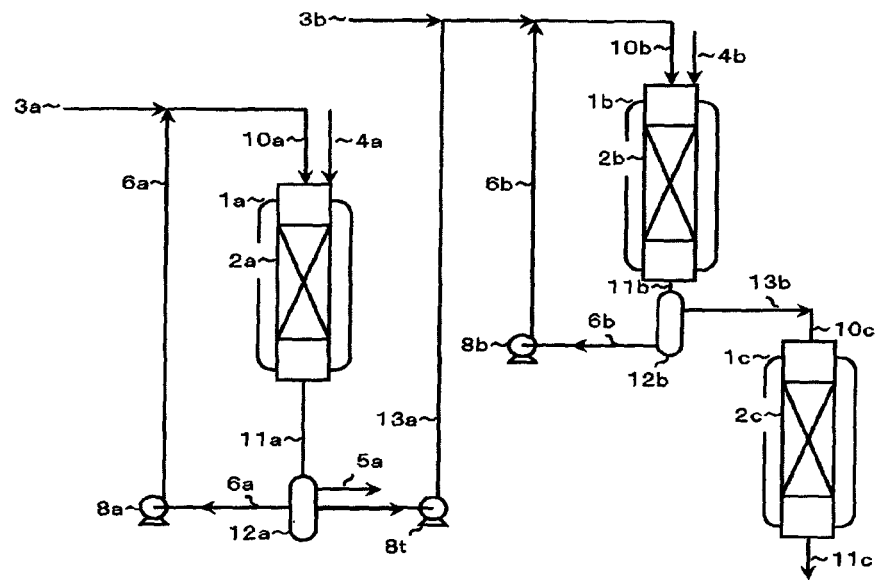
[Figure 6]
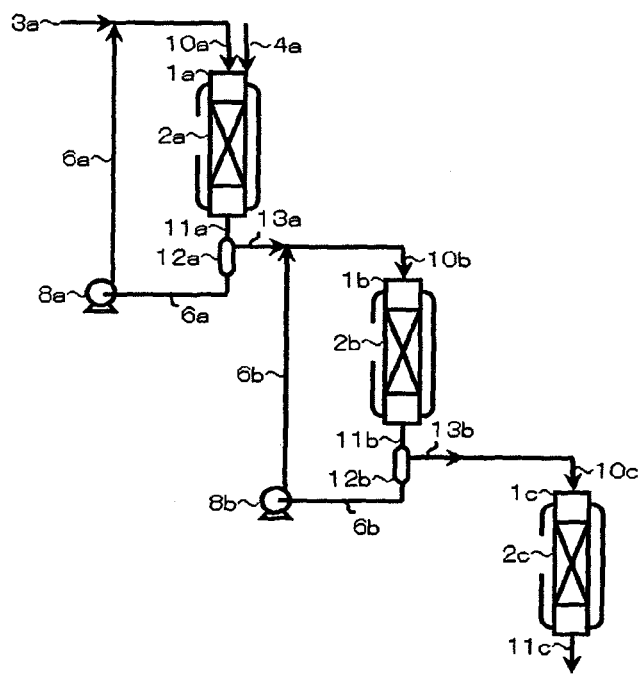

METHOD FOR PRODUCING α-HYDROXYISOBUTYRIC ACID AMIDE AND REACTOR

TECHNICAL FIELD

The present invention relates to a method for industrially producing an α-hydroxyisobutyric acid amide by hydration of an acetone cyanohydrin and a reaction apparatus. The α-hydroxyisobutyric acid amide is an important compound as a raw material for the production of corresponding hydroxy carboxylic acid ester or unsaturated carboxylic acid ester, and the development of a method for industrially stably producing an α-hydroxyisobutyric acid amide has great significance.

BACKGROUND ART

Various methods for producing an α-hydroxyisobutyric acid amide by hydration of an acetone cyanohydrin in the presence of a catalyst composed mainly of manganese oxide have been disclosed. For example, Patent Document 1 discloses that in hydration of an acetone cyanohydrin using manganese oxide, reaction results are improved by adding acetone to a reaction raw material consisting of acetone cyanohydrin and water, and that in this case, the conversion of acetone cyanohydrin is 99.0% and the yield of α-hydroxyisobutyric acid amide is 95%. However, according to the method described in Patent Document 1, the catalyst life is not sufficiently improved, and it is difficult to carry out the method at large-scale commercial plants.

Several improved methods relative to the method described in Patent Document 1 have been proposed. For example, a method in which an oxidizing agent such as oxygen and ozone is allowed to coexist (Patent Document 2), a method in which pH of a reaction raw material is adjusted (Patent Documents 3 and 4), a method in which a portion of a reaction product liquid is circulated in order to adjust pH of a reaction raw material (Patent Document 3), a method in which carbon dioxide is allowed to coexist (Patent Document 5), a method in which a catalyst is pretreated with a reduction solution prior to the reaction (Patent Document 6), and a method in which the reaction is performed under reduced pressure (Patent Document 7) are disclosed.

These methods respectively exert effects of improving catalytic activity or catalyst life, but it is difficult to stably maintain a high acetone cyanohydrin conversion for a long period of time using a reaction raw material containing an acetone cyanohydrin at a concentration of 30% by weight or more. For example, Patent Document 4 describes a working example in which a method of adjusting pH of a reaction raw material was combined with a method of allowing an oxidizing agent to coexist and a reaction raw material containing an acetone cyanohydrin at a concentration of 30.4% by weight was used, but the life defined as the time for the conversion to be reduced to less than 50% of that at the start is not more than 58 days.

Further, Patent Documents 8 and 9 disclose a method in which, even when the conversion of acetone cyanohydrin is low, unreacted acetone cyanohydrin in a reaction product liquid is thermally decomposed into acetone and hydrocyanic acid, and these substances are separated from the reaction product liquid and collected, and then acetone cyanohydrin is made therefrom again. However, this method is not economical because extra energy is required for a thermal decomposition reaction and an acetone cyanohydrin synthesis reaction.

PRIOR ART DOCUMENTS

Patent Documents

Patent Document 1: Japanese Laid-Open Patent Publication No. S52-222
Patent Document 2: Japanese Laid-Open Patent Publication No. H03-188054
Patent Document 3: Japanese Laid-Open Patent Publication No. H02-196763
Patent Document 4: Japanese National-phase PCT Laid-Open Patent Publication No. 2010-510276
Patent Document 5: Japanese Laid-Open Patent Publication No. 1107-076563
Patent Document 6: Japanese Laid-Open Patent Publication No. H02-298718
Patent Document 7: Japanese Laid-Open Patent Publication No. H04-149164
Patent Document 8: Japanese Laid-Open Patent Publication No. H06-172283
Patent Document 9: Japanese Laid-Open Patent Publication No. H06-184072

SUMMARY OF THE INVENTION

Problems to be Solved by the Invention

In general, synthesis of an acetone cyanohydrin by a reaction between hydrocyanic acid and acetone quantitatively proceeds in the presence of an alkali catalyst, and therefore, an acetone cyanohydrin at a high concentration of 50% by weight or more can be easily obtained. However, when hydration is performed using a reaction raw material containing an acetone cyanohydrin at a high concentration in the presence of a catalyst composed mainly of manganese oxide, the catalytic activity is rapidly reduced. For this reason, it is general to use a low-concentrated acetone cyanohydrin as a raw material. However, when a low-concentrated acetone cyanohydrin is used, the concentration of α-hydroxyisobutyric acid amide in a reaction product liquid obtained is also low, and a large amount of energy is consumed in the concentration/purification process.

The problem to be solved by the present invention is to provide a method for producing an α-hydroxyisobutyric acid amide by hydration of an acetone cyanohydrin in the presence of a catalyst composed mainly of manganese oxide, wherein the conversion of acetone cyanohydrin can be stably maintained at a high level for a long period of time even under severe conditions in which the α-hydroxyisobutyric acid amide is synthesized from a reaction raw material containing an acetone cyanohydrin at a concentration of 30% by weight or more.

Means for Solving the Problems

The present inventors diligently made researches in order to solve the above-described problem, and found that the reduction in the catalytic activity is mainly caused by elution of manganese as the main component of the catalyst and that the elution amount of manganese is closely related to the acetone cyanohydrin concentration in the reaction liquid. Further, the present inventors found that, according to the below-described present invention, the acetone cyanohydrin concentration in each reaction region can be decreased, the catalyst life can be improved, and the conversion of acetone cyanohydrin can be maintained at a high level for a significantly longer period of time and more stably compared to the prior art even under severe conditions in which the α-hydroxyisobutyric acid amide is synthesized from a reaction raw material containing an acetone cyanohydrin at a concentration of 30% by weight or more, and thus the present invention was achieved.

Specifically, the present invention is as follows:

<1> A method for producing α-hydroxyisobutyric acid amide by hydration of acetone cyanohydrin in the presence of a catalyst composed mainly of manganese oxide using a reaction apparatus in which at least two reaction regions are connected in series, wherein the method comprises:

a step (B) of cyclically supplying at least a portion of a reaction liquid withdrawn from at least one reaction region to a first reaction region (I) in the reaction apparatus; and a step (b1) of further cyclically supplying at least a portion of the reaction liquid withdrawn from at least one reaction region to at least one reaction region other than the first reaction region, and wherein an oxidizing agent is supplied to at least one reaction region in the reaction apparatus.

<2> A method for producing α-hydroxyisobutyric acid amide by hydration of acetone cyanohydrin in the presence of a catalyst composed mainly of manganese oxide using a reaction apparatus in which at least two reaction regions are connected in series, wherein the method comprises:

a step (A) of supplying a reaction raw material liquid containing the acetone cyanohydrin dividedly to a first reaction region (I) and at least one reaction region other than the first reaction region in the reaction apparatus;

a step (B) of cyclically supplying at least a portion of a reaction liquid withdrawn from at least one reaction region to the first reaction region (I) in the reaction apparatus; and a step (b1) of further cyclically supplying at least a portion of the reaction liquid withdrawn from at least one reaction region to at least one reaction region other than the first reaction region, and wherein an oxidizing agent is supplied to at least one reaction region in the reaction apparatus.

<3> The method for producing α-hydroxyisobutyric acid amide according to item <1> or <2>, wherein at least a part of the step (b1) is conducted at a position nearer to an outlet of the reaction apparatus compared to a reaction region that is nearest to an inlet of the reaction apparatus among at least one reaction region from which the reaction liquid is withdrawn in order to cyclically supply the reaction liquid to the first reaction region (I).

<4> The method for producing α-hydroxyisobutyric acid amide according to item <3>, wherein at least a part of the step (b1) is conducted at a position nearer to the outlet of the reaction apparatus compared to every reaction region from which the reaction liquid is withdrawn in order to cyclically supply the reaction liquid to the first reaction region (I).

<5> The method for producing α-hydroxyisobutyric acid amide according to any one of items <1> to <4>, wherein in the step (b1), said at least one reaction region other than the first reaction region is identical to said at least one reaction region.

<6> The method for producing α-hydroxyisobutyric acid amide according to any one of items <1> to <5>, wherein the number of the reaction regions connected in series is 7 or less.

<7> The method for producing α-hydroxyisobutyric acid amide according to item <2>, wherein the number of the reaction regions to which the reaction raw material liquid containing the acetone cyanohydrin is supplied in the step (A) is 5 or less.

<8> The method for producing α-hydroxyisobutyric acid amide according to item <1>, wherein the method comprises a step of supplying a reaction raw material liquid containing the acetone cyanohydrin, and wherein the ratio of the acetone cyanohydrin in the total amount of the reaction raw material liquid is 30% by weight or more.

<9> The method for producing α-hydroxyisobutyric acid amide according to item <2>, wherein the ratio of the acetone cyanohydrin in the total amount of the reaction raw material liquid is 30% by weight or more.

<10> The method for producing α-hydroxyisobutyric acid amide according to any one of items <1> to <9>, wherein the ratio of the acetone cyanohydrin in the total amount of a reaction region supply liquid (C) to be supplied to said at least two reaction regions is 25% by weight or less, and wherein the reaction region supply liquid (C) is supplied to each of the reaction regions and is at least one selected from the group consisting of the reaction raw material liquid, a diluent, and a reaction liquid flowing out or withdrawn from the reaction regions.

<11> The method for producing α-hydroxyisobutyric acid amide according to any one of items <1> to <10>, wherein an oxygen-containing gas is used as the oxidizing agent, and wherein the oxygen concentration in the oxygen-containing gas is 2 to 50% by volume.

<12> The method for producing α-hydroxyisobutyric acid amide according to item <11>, wherein the gas in the reaction region is exchanged by supplying a gas having a sufficient oxygen concentration while withdrawing a gas having a reduced oxygen concentration.

<13> The method for producing α-hydroxyisobutyric acid amide according to any one of items <1> to <12>, wherein the catalyst composed mainly of manganese oxide is manganese dioxide.

<14> The method for producing α-hydroxyisobutyric acid amide according to any one of items <1> to <13>, wherein the catalyst composed mainly of manganese oxide comprises a compound represented by composition formula: $Mn_aK_bM_cO_d$
wherein: Mn represents manganese; K represents potassium; O represents oxygen; M represents at least one element selected from V, Sn and Bi; and regarding the atomic ratio of each element, when a=1, b is 0.005 to 0.5, c is 0.001 to 0.1, and d is 1.7 to 2.0.

<15> A reaction apparatus for producing α-hydroxyisobutyric acid amide by hydration of acetone cyanohydrin in the presence of a catalyst composed mainly of manganese oxide, wherein the reaction apparatus has at least two reaction regions connected in series and further has:

(a) a piping for supplying a reaction raw material liquid containing the acetone cyanohydrin dividedly to a first reaction region (I) and at least one reaction region other than the first reaction region in the reaction apparatus; and/or (b) a piping for cyclically supplying at least a portion of a reaction liquid withdrawn from at least one reaction region to the first reaction region (I) in the reaction apparatus, and wherein the reaction apparatus further has a piping for supplying an oxidizing agent to at least one reaction region.

<16> The reaction apparatus according to item <15>, further having a piping for cyclically supplying at least a portion of the reaction liquid withdrawn from at least one reaction region to at least one reaction region other than the first reaction region.

<17> The reaction apparatus according to item <16>, which has at least one circulation loop composed of: at least one reaction region other than the first reaction region; at least one reaction region from which the reaction liquid is withdrawn in order to cyclically supply the reaction liquid to said reaction region; and a piping for connecting the former reaction region and the latter reaction region, wherein both the at least one reaction region other than the first reaction region and the at least one reaction region from which the reaction liquid is withdrawn, which constitute at least one circulation loop (V) among said circulation loop, are placed at a position nearer to an outlet of the reaction apparatus compared to a reaction region that is nearest to an inlet of the reaction apparatus among at least one reaction region from which the reaction liquid is withdrawn in order to cyclically supply the reaction liquid to the first reaction region (I).

<18> The reaction apparatus according to item <17>, wherein both the at least one reaction region other than the first reaction region and the at least one reaction region from which the reaction liquid is withdrawn, which constitute the circulation loop (V), are placed at a position nearer to the outlet of the reaction apparatus compared to every reaction region from which the reaction liquid is withdrawn in order to cyclically supply the reaction liquid to the first reaction region (I).

<19> The reaction apparatus according to any one of items <15> to <18>, wherein an equipment for withdrawing the oxidizing agent is connected to the first reaction region (I) and/or a position between at least one reaction region other than the first reaction region and another reaction region, or the first reaction region (I) and/or the middle portion of at least one reaction region other than the first reaction region.

Advantageous Effect of the Invention

According to the present invention, when producing an α-hydroxyisobutyric acid amide by hydration of an acetone cyanohydrin in the presence of a catalyst composed mainly of manganese oxide, the conversion of acetone cyanohydrin can be maintained at a high level for a significantly longer period of time and more stably compared to the prior art even under severe conditions in which the α-hydroxyisobutyric acid amide is synthesized from a reaction raw material containing an acetone cyanohydrin at a concentration of 30% by weight or more. Therefore, the present invention has great industrial significance.

BRIEF DESCRIPTION OF THE DRAWINGS

FIG. 1 is a process flow diagram showing an example of the reaction apparatus of the present invention which dividedly supplies ACH (acetone cyanohydrin) and cyclically supplies a reaction liquid.

FIG. 2 is a process flow diagram showing another example of the reaction apparatus of the present invention which dividedly supplies ACH and cyclically supplies a reaction liquid (a system in which a plurality of reaction regions are provided in a reactor).

FIG. 3 is a process flow diagram showing another example of the reaction apparatus of the present invention which dividedly supplies ACH and cyclically supplies a reaction liquid (a system in which the temperature of the reaction liquid withdrawn is adjusted using a heat exchanger and then the reaction liquid is returned to the original reaction region).

FIG. 4 is a process flow diagram showing another example of the reaction apparatus of the present invention which dividedly supplies ACH and cyclically supplies a reaction liquid (a system in which a circulating liquid is returned to a plurality of reaction regions).

FIG. 5 is a process flow diagram showing the reaction apparatus of Example 1.

FIG. 6 is a process flow diagram showing the reaction apparatus of Example 3.

EMBODIMENTS FOR CARRYING OUT THE INVENTION

Hereinafter, the present invention will be described in detail.

The reaction apparatus of the present invention, which can be used for the production of an α-hydroxyisobutyric acid amide (hereinafter referred to as HBD in principle), is a reaction apparatus in which at least two reaction regions are connected in series. In this regard, the reaction region refers to an independent section in which a catalyst composed mainly of manganese oxide, which has catalytic activity in hydration of an acetone cyanohydrin (hereinafter referred to as ACH in principle), exists. In this reaction region, ACH reacts with water and is converted to HBD that is an objective substance. This reaction region may be a reactor filled with the catalyst composed mainly of manganese oxide, or may be each of several catalyst zones (catalyst layers) separately provided in one reactor.

In the method for producing HBD of the present invention, the number of reaction regions connected in series is not particularly limited as long as it is 2 or more. However, when there are too many reaction regions connected in series, the apparatus becomes complicated and it becomes complicated to control a reaction in each of the reaction regions. Therefore, from a practical viewpoint, the number of the reaction regions connected in series is preferably 2 to 7, and particularly preferably 3 to 5. Further, the upper limit of the total number of reaction regions is not particularly limited. Moreover, a reaction region, which has a parallel relationship with the reaction regions connected in series, may exist.

In the method for producing HBD of the present invention, the reaction raw material liquid refers to an ACH-containing raw material liquid supplied to the reaction regions in the reaction apparatus via a supply line of reaction raw material liquid. That is, ACH is supplied to the reaction regions via the supply line of reaction raw material liquid as the reaction raw material liquid. The HBD concentration in the reaction product liquid flowing out from the last reaction region is determined by the ACH concentration in the reaction raw material liquid and the conversion of hydration. When the aforementioned HBD concentration is low, a large amount of energy is consumed in processes of condensation and purification, resulting in increase in the HBD purification cost. From the viewpoint of the above-described HBD purification cost, it is preferred to employ a high ACH concentration in the reaction raw material liquid. As described later, in the case of supplying the reaction raw material liquid dividedly to a plurality of reaction regions, the reaction raw material liquid is supplied via a plurality of supply lines of reaction raw material liquid. The ACH concentration in the reaction raw material liquid supplied to a plurality of reaction regions may vary.

In general, an ACH synthesis reaction using hydrocyanic acid and acetone as raw materials quantitatively proceeds in the presence of an alkali catalyst, and ACH is obtained at a concentration of 50% by weight or more. In the method for producing HBD of the present invention, as the reaction raw material liquid containing ACH to be used in the HBD production, a reaction liquid containing ACH at a high concentration obtained by the above-described ACH synthesis reaction may be used. Alternatively, a liquid obtained by mixing a diluent with the reaction liquid containing ACH at a high concentration obtained by the above-described ACH synthesis reaction may be used as the reaction raw material liquid containing ACH. Specifically, the ACH concentration in the reaction raw material liquid to be used in the HBD production may be adjusted to the above-described predetermined concentration using a diluent according to need. Like the prior art, as the diluent, an excess amount of water, which is a raw material for hydration, may be used, and acetone, which h functions to suppress an ACH decomposition reaction that is a side reaction, may also be used. Other than water and acetone, amides such as formamide, dimethylformamide, dimethylacetamide and HBD that is a reaction product can also be used as the diluent. As the diluent, the above-described compounds may be used solely, or two or more of them may be used in combination. Among them, as the diluent, water, acetone, HBD and formamide are preferred, and among amides, HBD is particularly preferred. In the present invention, it is defined that the reaction liquid flowing out or withdrawn from the reaction region is not included in the diluent, because it contains a certain quantity of unreacted ACH.

In the case of using the liquid obtained by mixing the diluent with the reaction liquid containing ACH at a high concentration obtained by the ACH synthesis reaction as the reaction raw material liquid containing ACH, the timing and method of mixing the diluent are not particularly limited. For example, the reaction raw material liquid containing ACH can be obtained by a method in which the reaction liquid containing ACH at a high concentration is mixed with the diluent in a storage tank to be diluted to have a desired ACH concentration. Further, it is also possible to obtain the reaction raw material liquid containing ACH by joining the reaction liquid containing ACH at a high concentration obtained by the ACH synthesis into a supply line of diluent immediately prior to be directly supplied to any of reaction regions.

In the present invention, when the reaction raw material liquid containing ACH is obtained by mixing the reaction liquid containing ACH at a high concentration obtained by the ACH synthesis reaction with the diluent, it is defined that the ratio of ACH in the total amount of the reaction raw material liquid refers to the weight fraction of ACH relative to the total weight of the reaction liquid containing ACH at a high concentration obtained by the ACH synthesis reaction and the diluent.

Further, when the reaction liquid containing ACH at a high concentration obtained by the ACH synthesis reaction is used as the reaction raw material liquid, it is defined that the ratio of ACH in the total amount of the reaction raw material liquid refers to the weight fraction of ACH relative to the total weight of the reaction liquid.

As described above, in the method for producing HBD of the present invention, the reaction raw material liquid may be supplied dividedly to a plurality of reaction regions. Further, the ACH concentration in the reaction raw material liquid supplied to the respective reaction regions may be the same or may vary. When the reaction raw material liquid is supplied to a plurality of reaction regions, the ratio of ACH in the total amount of the reaction raw material liquid refers to the ratio (weight fraction) of the total weight of ACH contained in the reaction raw material liquid supplied to the respective reaction regions in the total weight of the reaction raw material liquid supplied to the respective reaction regions.

The ratio of ACH in the total amount of the reaction raw material liquid is preferably 30% by weight or more, more preferably 30% by weight to 83% by weight, and most preferably 35% by weight to 53% by weight.

In the HBD production of the present invention, as described above, the ratio of ACH in the total weight of the reaction raw material liquid to be used in the HBD production is preferably 30% by weight or more, but the ACH concentration in the below-described reaction region supply liquid (C) is lower than the ACH concentration in the reaction raw material liquid. The reaction region supply liquid (C) refers to a liquid to be supplied to each of the reaction regions and consists of at least one selected from the reaction raw material liquid, the diluent, and the reaction liquid flowing out or withdrawn from the reaction regions. In the present invention, the ratio of the amount of ACH in the total amount of the reaction region supply liquid (C) is preferably 25% by weight or less. In this regard, the total amount of the reaction region supply liquid (C) means the sum of the amounts of the reaction region supply liquid (C) supplied to the respective reaction regions. Further, hydration is performed with the ACH concentration in the reaction region supply liquid (C) supplied to all the reaction regions in the reaction apparatus being adjusted to preferably 25% by weight or less, more preferably 20% by weight or less, and particularly preferably 15% by weight or less. This is because, by reduction in the ACH concentration in the reaction liquid at the inlet of the reaction region, not only an effect of simply reducing the reaction load of the catalyst is exerted, but also a very important effect of reducing elution of manganese ion associated with the reaction is exerted. Eluted manganese ion is precipitated on the surface of the catalyst positioned downstream of the portion where manganese is eluted as a form of the manganese oxide or the manganese hydroxide that has low reactivity or no reactivity, and this may cause reduction in catalyst life. Further, precipitation of the eluted manganese ion may cause bonding of each particle of the catalyst together to interfere with the catalysis exchange work, or may cause a breakdown of a reaction product liquid delivery pump or pump for the purification system or blocking of piping, resulting in the troubles of the plant operation.

In the method for producing HBD of the present invention, the period for performing hydration with the ratio of the amount of ACH in the total amount of the reaction region supply liquid (C) being adjusted to 25% by weight or less is not particularly limited, but it is preferably at least a half or more of the entire period of hydration, and particularly preferably 80% or more of the entire period of hydration.

Only by a simple dilution operation, it is impossible to obtain a highly-concentrated HBD solution corresponding to the ACH concentration of the reaction raw material liquid to be used in the HBD production, and it is required to perform an operation of cyclically supplying the reaction liquid, and it is preferred to further combine therewith an operation of dividedly supplying ACH. Specifically, the method for producing HBD of the present invention is carried out according to any one of the below-described two embodiments:
[Embodiment 1]: cyclically supplying the reaction liquid

[Embodiment 2]: cyclically supplying the reaction liquid and dividedly supplying ACH Hereinafter, the respective embodiments will be described in detail.

The first embodiment of the method for producing HBD of the present invention (hereinafter referred to as "Embodiment 1" in principle) is a method for producing an α-hydroxyisobutyric acid amide by hydration of an acetone cyanohydrin in the presence of a catalyst composed mainly of manganese oxide using a reaction apparatus in which at least two reaction regions are connected in series, wherein the method comprises:

a step (B) of cyclically supplying at least a portion of a reaction liquid withdrawn from at least one reaction region to a first reaction region (I) in the reaction apparatus; and a step (b1) of further cyclically supplying at least a portion of the reaction liquid withdrawn from at least one reaction region to at least one reaction region other than the first reaction region, and wherein an oxidizing agent is supplied to at least one reaction region in the reaction apparatus.

In Embodiment 1, at least a portion of the reaction liquid withdrawn from at least one reaction region is cyclically used. This makes it possible to reduce the ACH concentration in the reaction region supply liquid (C) supplied to the respective reaction regions to improve the catalyst life and to inhibit the troubles of the plant operation, and at the same time, the HBD concentration in the reaction liquid at the outlet of the last reaction region can be increased. Moreover, cyclical use of the reaction liquid has the effect to adjust pH of the reaction region supply liquid (C) supplied to the reaction regions to 4 or more, which is preferable from the viewpoint of the catalyst life, and therefore, the catalyst life can be extended by dual effect, i.e., the effect exerted by pH adjustment and the effect of suppressing elution of manganese by means of adjustment of the ACH concentration.

In the step (B), at least one reaction region from which the reaction liquid is withdrawn in order to cyclically supply at least a portion of the reaction liquid to the first reaction region (I) may be the first reaction region itself or a reaction region at a position nearer to the outlet of the reaction apparatus compared to the first reaction region (downstream). Specifically, it may be any reaction region in the reaction apparatus of the present invention as long as it does not interrupt the step (b1). In the step (b1), at least one reaction region from which the reaction liquid is withdrawn in order to cyclically supply at least a portion of the reaction liquid to at least one reaction region other than the first reaction region may be the at least one reaction region other than the first reaction region itself to which the reaction liquid is cyclically supplied or a reaction region at a position nearer to the outlet of the reaction apparatus compared to the at least one reaction region other than the first reaction region (downstream).

In the step (B), at least one reaction region from which the reaction liquid is withdrawn in order to cyclically supply at least a portion of the reaction liquid to the first reaction region (I) may be a plurality of reaction regions. Further, in the step (b1), at least one reaction region from which the reaction liquid is withdrawn in order to cyclically supply at least a portion of the reaction liquid to at least one reaction region other than the first reaction region may be a plurality of reaction regions. The at least one reaction region from which the reaction liquid is withdrawn to cyclically supply it in the step (B) and the at least one reaction region from which the reaction liquid is withdrawn to cyclically supply it in the step (b1) may be the same or different from each other, but preferably different from each other.

In Embodiment 1, it is more preferred to cyclically supply the reaction liquid to at least one reaction region other than the first reaction region in addition to the first reaction region (I) from the viewpoint that the ACH concentration in the reaction region supply liquid (C) supplied to the reaction regions can be more easily reduced, resulting in decrease in elution of manganese ion and that it is possible to build an efficient process with a smaller number of reaction regions. When the reaction liquid is cyclically supplied to reaction regions other than the first reaction region, with respect to at least one reaction region, it is desirable that the reaction liquid is withdrawn from a reaction region (named as the secondary opening for withdrawing the reaction liquid) provided at a position nearer to the outlet of the reaction apparatus (downstream) compared to a reaction region (named as the primary opening for withdrawing the reaction liquid) from which the reaction liquid is withdrawn to cyclically supply it to the first reaction region (I), and that the reaction liquid is supplied to any reaction region provided at a position between the primary opening for withdrawing the reaction liquid and the secondary opening for withdrawing the reaction liquid or to the reaction region itself that provides the secondary opening for withdrawing the reaction liquid.

In Embodiment 1, it is possible to provide a plurality of primary openings for withdrawing the reaction liquid to the reaction apparatus and to cyclically supply the reaction liquid from a plurality of reaction regions to the first reaction region (I). In this case, a desirable positional relationship between the plurality of primary openings for withdrawing the reaction liquid, reaction regions other than the first reaction region to which the reaction liquid is cyclically supplied and the secondary opening for withdrawing the reaction liquid is as described below. Specifically, in Embodiment 1, at least one pair of the reaction regions other than the first reaction region to which the reaction liquid is cyclically supplied and the secondary opening for withdrawing the reaction liquid is desirably provided at a position nearer to the outlet of the reaction apparatus (downstream) compared to a primary opening for withdrawing the reaction liquid nearest to the inlet of the reaction apparatus among the plurality of primary openings for withdrawing the reaction liquid provided. More desirably, it is provided at a position nearer to the outlet of the reaction apparatus (downstream) compared to the first primary opening for withdrawing the reaction liquid in which the integrated quantity of the reaction liquid withdrawn from each of the plurality of primary openings for withdrawing the reaction liquid provided exceeds 50% of the total amount of the reaction liquid withdrawn from all the plurality of primary openings for withdrawing the reaction liquid provided. Most desirably, at least one pair of the reaction regions other than the first reaction region to which the reaction liquid is cyclically supplied and the secondary opening for withdrawing the reaction liquid is provided at a position nearer to the outlet of the reaction apparatus (downstream) compared to all the primary openings for withdrawing the reaction liquid. In this way, in addition to a reaction liquid circulation pathway composed of the first reaction region (I), the reaction regions from which the reaction liquid is withdrawn to cyclically supply it to the first reaction region (I) and a circulation line, another reaction liquid circulation pathway, which is independent to some extent, is provided at a position nearer to the outlet of the reaction apparatus. In this case, reaction conditions of reaction regions existing in the respective reaction liquid circulation pathways can be independently controlled and optimized, and it is easier to maximize the performance of the filled catalyst.

In Embodiment 1, the ACH concentration in the reaction region supply liquid (C) supplied to the reaction regions is adjusted by cyclically supplying the reaction liquid itself in which a compound having the elution effect such as water, acetone, HBD and formamide is contained, and therefore it is not necessary to additionally use a diluent. However, from a practical viewpoint, the ACH concentration in the reaction region supply liquid (C) supplied to the first reaction region (I) is preferably adjusted by using both a diluent and the cyclically-supplied reaction liquid. Other than water and acetone, amides such as formamide, dimethylformamide, dimethylacetamide and HBD that is a reaction product can also be used as the diluent. As the diluent, the above-described compounds may be used solely, or two or more of them may be used in combination. Among them, as the diluent, water, acetone, HBD and formamide are preferred, and among amides, HBD is particularly preferred.

The amount of the reaction liquid to be cyclically supplied is defined by the below-described formula (1) as the circulation ratio based on the supply rate of the cyclically-supplied reaction liquid (X) and the supply rate of the reaction region supply liquid (C) supplied to the reaction regions (Y):

Circulation ratio=$(X)/((Y)-(X))$  formula (1)

The circulation ratio in Embodiment 1 is not particularly limited.

In Embodiment 1, the molar ratio between water and ACH in the reaction region supply liquid (C) supplied to all the reaction regions in the reaction apparatus is not particularly limited, but the amount of water is preferably 1 to 200 mol, and particularly preferably 10 to 100 mol relative to 1 mol of ACH. The molar ratio between acetone and ACH is not particularly limited, but the amount of ACH is preferably 0.1 to 10 mol relative to 1 mol of acetone.

In Embodiment 1, the supply amounts of water and ACH contained in the reaction raw material liquid supplied to the reaction apparatus relative to the total weight of the catalyst filled in all the reaction regions in the reaction apparatus are not particularly limited, but in the case of water, it is supplied preferably at a rate of 0.0625 to 0.625 g/hr, more preferably at a rate of 0.125 to 0.25 g/hr, and most preferably at a rate of 0.15 to 0.225 g/hr relative to 1 g of the catalyst. In the case of ACH, it is supplied preferably at a rate of 0.05 to 0.5 g/hr, more preferably at a rate of 0.1 to 0.2 g/hr, and most preferably at a rate of 0.12 to 0.18 g/hr relative to 1 g of the catalyst.

As the method for producing HBD of the present invention, the below-described second embodiment is particularly preferred. The second embodiment of the method for producing HBD of the present invention is a method for producing an α-hydroxyisobutyric acid amide by hydration of an acetone cyanohydrin in the presence of a catalyst composed mainly of manganese oxide using a reaction apparatus in which at least two reaction regions are connected in series, wherein the method comprises:

a step (A) of supplying a reaction raw material liquid containing the acetone cyanohydrin dividedly to a first reaction region (I) and at least one reaction region other than the first reaction region in the reaction apparatus;

a step (B) of cyclically supplying at least a portion of a reaction liquid withdrawn from at least one reaction region to the first reaction region (I) in the reaction apparatus; and a step (b1) of further cyclically supplying at least a portion of the reaction liquid withdrawn from at least one reaction region to at least one reaction region other than the first reaction region, and wherein an oxidizing agent is supplied to at least one reaction region in the reaction apparatus.

In the above-described Embodiment 2, at least one reaction region other than the first reaction region in the step (A), i.e., at least one reaction region other than the first reaction region to which the reaction raw material liquid is dividedly supplied may be a plurality of reaction regions. Further, at least one reaction region in the step (b1), i.e., at least one reaction region other than the first reaction region to which at least a portion of the reaction liquid withdrawn from at least one reaction region is cyclically supplied may be a plurality of reaction regions. Moreover, the at least one reaction region other than the first reaction region in the step (A) and the at least one reaction region other than the first reaction region in the step (b1) may be the same or different from each other.

Specifically, it is particularly preferred to dividedly supply ACH in addition to cyclically supplying at least a portion of the reaction liquid withdrawn from at least one reaction region as explained above. This is because, in addition to the above-described advantages of Embodiment 1, when compared to Embodiment 1, the ACH concentration in the reaction region supply liquid (C) supplied to the respective reaction regions can be decreased more efficiently, and the HBD concentration in the reaction product liquid flowing out from the last reaction region can be efficiently increased with a smaller number of reaction regions, leading to building of a more efficient process. Hereinafter, the second embodiment of the method for producing HBD of the present invention (hereinafter sometimes referred to as "combination method") will be described in detail.

As the second embodiment, for example, when hydration of ACH is carried out using a reaction apparatus in which three reaction regions are connected in series, ACH can be dividedly supplied to the first reaction region and the second reaction region. Alternatively, ACH can be dividedly supplied to the first reaction region and the third reaction region. Alternatively, ACH can be dividedly supplied to all the three reaction regions.

Embodiment 2 has the following three advantages: the ACH concentration in the reaction region supply liquid (C) supplied to the reaction regions can be easily decreased; the difference of the reaction load between the respective reaction regions to which ACH is supplied can be decreased; and the HBD concentration in the reaction liquid at the outlet of the last reaction region can be maintained at a high level even when the ACH concentration in the reaction regions is low. These advantages will be explained below.

Firstly, by reduction in the ACH concentration in the reaction region supply liquid (C) supplied to the reaction regions, not only an effect of simply reducing the reaction load of the catalyst, but also a very important effect of reducing elution of manganese ion associated with the reaction is exerted as described above. Specifically, by reducing the ACH concentration in the reaction region supply liquid (C) supplied to the reaction regions by means of dividedly supplying ACH, elution of manganese ion can be suppressed, the catalyst life can be improved, and the number of the plant operation troubles can be decreased.

The second advantage will be explained below. As known well, in the case of a simple continuous flow-type reaction in which a reaction raw material is not dividedly supplied, the distance in which the reaction raw material is passed through catalyst-filled reaction regions is not directly proportional to the conversion, and a major part of the reaction is progressed at reaction regions in the former half through which the reaction raw material is passed, and the ratio of the reaction progressed at reaction regions in the latter half is small. Hydration of ACH is no exception. Therefore, by dividedly supplying ACH to two or more reaction regions, the difference of the reaction load between the respective reaction regions can be reduced, and it can be expected that the catalyst life can be extended thereby.

The third advantage will be explained below. In the method of Embodiment 2, after a portion of ACH in the first reaction region to which ACH is supplied becomes HBD, ACH is added to the second reaction region or later. Therefore, the HBD concentration in the reaction liquid at the outlet of each reaction region can be increased in a stepwise manner while the ACH concentration in the reaction region supply liquid (C) supplied to the reaction regions is maintained at a low level. For example, when a reaction is performed using a reaction raw material with the ACH concentration of 25% by weight in a one-pass reaction apparatus in which ACH is not dividedly supplied, even if the reaction is completely progressed, the HBD concentration in the reaction product liquid at the outlet of the last reaction region is no more than 30% by weight. Meanwhile, according to the above-described method for dividedly supplying ACH, even when the ACH concentration in the reaction region supply liquid (C) supplied to all the reaction regions in the reaction apparatus is adjusted to 25% by weight or less, the HBD concentration in the reaction product liquid flowing out from the last reaction region can be increased to, for example, 40% by weight or more. Therefore, the cost for separation of HBD from water, acetone or the like in the purification system can be reduced, and it is very economical.

Thus, by dividedly supplying ACH, even when the ACH concentration in the reaction raw material liquid to be used in the HBD production is 30% by weight or more, the ACH concentration in the reaction region supply liquid (C) supplied to the reaction regions can be reduced efficiently, and the difference of the reaction load between the respective reaction regions to which ACH is supplied can be decreased, and therefore the catalyst life can be more extended compared to the conventional methods. Moreover, even when the ACH concentration in the reaction region supply liquid (C) supplied to the reaction regions is low, the HBD concentration in the reaction liquid flowing out from the last reaction region, i.e., the reaction product liquid at the outlet of the reaction apparatus can be increased, and therefore it is more economical compared to the conventional reaction processes.

In Embodiment 2, the number of reaction regions to which ACH is dividedly supplied is not particularly limited as long as it is 2 or more. However, when there are too many reaction regions to which ACH is dividedly supplied, the apparatus becomes complicated and it becomes complicated to control a reaction in each of the reaction regions. Therefore, from a practical viewpoint, the number of the reaction regions is preferably 2 to 5, and particularly preferably 3 to 4.

In Embodiment 2, the ACH distribution ratio (ACH division ratio) between the reaction regions to which ACH is dividedly supplied is not particularly limited, but it is preferred that the ratio of the amount of ACH supplied to the first reaction region relative to the total amount of ACH supplied to the reaction apparatus is 50 to 98% by weight, and that the remaining ACH is dividedly supplied to the second reaction region or later. This is because, since the reaction liquid is cyclically supplied to the first reaction region in Embodiment 2, even when the amount of ACH dividedly supplied to the first reaction region is increased, the ACH concentration can be reduced more easily compared to the method of only dividedly supplying ACH, and in this way, the HBD concentration in the reaction liquid at the outlet of the last reaction region can be increased efficiently with a smaller number of reaction regions.

Also in Embodiment 2, it is more preferred to cyclically supply the reaction liquid to at least one reaction region other than the first reaction region in addition to the first reaction region (I) from the viewpoint that the ACH concentration in the reaction region supply liquid (C) supplied to the reaction regions can be more easily reduced, resulting in decrease in elution of manganese ion and that it is possible to build an efficient process with a smaller number of reaction regions. Moreover, it is particularly preferred to cyclically supply the reaction liquid to the reaction regions to which ACH is dividedly supplied. When the reaction liquid is cyclically supplied to reaction regions other than the first reaction region, it is desirable that the at least a portion of reaction liquid is withdrawn from a reaction region (named as the secondary opening for withdrawing the reaction liquid) provided at a position nearer to the outlet of the reaction apparatus (downstream) compared to a reaction region (named as the primary opening for withdrawing the reaction liquid) from which the reaction liquid is withdrawn to cyclically supply to the first reaction region (I), and supplied to any reaction region provided at a position between the primary opening for withdrawing the reaction liquid and the secondary opening for withdrawing the reaction liquid or to the reaction region itself that provides the secondary opening for withdrawing the reaction liquid.

In Embodiment 2, it is possible to provide a plurality of primary openings for withdrawing the reaction liquid to the reaction apparatus and to cyclically supply the reaction liquid from a plurality of reaction regions to the first reaction region (I). In this case, a desirable positional relationship between the plurality of primary openings for withdrawing the reaction liquid, reaction regions other than the first reaction region to which the reaction liquid is cyclically supplied and the secondary opening for withdrawing the reaction liquid is as described below. Specifically, in Embodiment 2, at least one pair of the reaction regions other than the first reaction region to which the reaction liquid is cyclically supplied and the secondary opening for withdrawing the reaction liquid is desirably provided at a position nearer to the outlet of the reaction apparatus (downstream) compared to a primary opening for withdrawing the reaction liquid nearest to the inlet of the reaction apparatus among the plurality of primary openings for withdrawing the reaction liquid provided. More desirably, it is provided at a position nearer to the outlet of the reaction apparatus (downstream) compared to the first primary opening for withdrawing the reaction liquid in which the integrated quantity of the reaction liquid withdrawn from each of the plurality of primary openings for withdrawing the reaction liquid provided exceeds 50% of the total amount of the reaction liquid withdrawn from all the plurality of primary openings for withdrawing the reaction liquid provided. Most desirably, at least one pair of the reaction regions other than the first reaction region to which the reaction liquid is cyclically supplied and the secondary opening for withdrawing the reaction liquid is provided at a position nearer to the outlet of the reaction apparatus (downstream) compared to all the primary openings for withdrawing the reaction liquid. In this way, in addition to a reaction liquid circulation pathway composed of the first reaction region (I), the reaction regions from which the reaction liquid is withdrawn to cyclically supply it to the first reaction region (I) and a circulation line, another reaction liquid circulation pathway, which is independent to some extent, is provided at a position nearer to the outlet of the reaction apparatus. In this case, reaction conditions of reaction regions existing in the respective reaction liquid circulation pathways can be independently controlled and optimized, and it is easier to maximize the performance of the filled catalyst.

In Embodiment 2, the ACH concentration in the reaction region supply liquid (C) supplied to the reaction regions is adjusted by cyclically supplying the reaction liquid itself in which a compound having the elution effect such as water, acetone, HBD and formamide is contained, and therefore it is not necessary to use the above-described diluent in addition to the reaction liquid in order to adjust the ACH concentration. However, from a practical viewpoint, the ACH concentration in the reaction region supply liquid (C) supplied to the first reaction region (I) is preferably adjusted by using both the diluent and the cyclically-supplied reaction liquid because in this case the circulation ratio explained later can be controlled within a preferred range. Other than water and acetone, amides such as formamide, dimethylformamide, dimethylacetamide and HBD that is a reaction product can also be used as the diluent. As the diluent, the above-described compounds may be used solely, or two or more of them may be used in combination. Among them, as the diluent, water, acetone, HBD and formamide are preferred, and among amides, HBD is particularly preferred.

In Embodiment 2, the molar ratio between water and ACH in the reaction region supply liquid (C) supplied to all the reaction regions in the reaction apparatus is not particularly limited, but the amount of water is preferably 1 to 200 mol, and particularly preferably 10 to 100 mol relative to 1 mol of ACH. The molar ratio between acetone and ACH is not particularly limited, but the amount of ACH is preferably 0.1 to 10 mol relative to 1 mol of acetone.

In Embodiment 2, the total supply amounts of water and ACH contained in the reaction raw material liquid supplied to the reaction apparatus relative to the total weight of the catalyst filled in all the reaction regions in the reaction apparatus are not particularly limited, but in the case of water, it is supplied preferably at a rate of 0.0625 to 0.625 g/hr, more preferably at a rate of 0.125 to 0.25 g/hr, and most preferably at a rate of 0.15 to 0.225 g/hr relative to 1 g of the catalyst. In the case of ACH, it is supplied preferably at a rate of 0.05 to 0.5 g/hr, more preferably at a rate of 0.1 to 0.2 g/hr, and most preferably at a rate of 0.12 to 0.18 g/hr relative to 1 g of the catalyst.

The amount of the reaction liquid to be cyclically supplied is defined by the below-described formula (1) as the circulation ratio based on the supply rate of the cyclically-supplied reaction liquid (X) and the supply rate of the reaction region supply liquid (C) supplied to the reaction regions (Y):

$$\text{Circulation ratio} = (X)/((Y)-(X)) \quad \text{formula (1)}$$

The circulation ratio in Embodiment 2 is not particularly limited, but when represented by the volume velocity ratio, it is preferably 0.5 to 50, and particularly preferably 1 to 20. The circulation ratio is a factor which affects the ACH concentration in the reaction region supply liquid (C) supplied to the reaction regions, and the larger the circulation ratio is, the longer the catalyst life is. However, when the ratio exceeds 50, the amount of the liquid passing through the reaction regions is increased, and this may lead to reduction in reaction performance such as reduction in the conversion of ACH and increase in the pressure loss.

Thus, in Embodiment 2, it is possible to increase the HBD concentration in the reaction liquid at the outlet of the last reaction region more efficiently with a smaller number of reaction regions compared to the method in which only circulating supply of the reaction product liquid is performed (Embodiment 1), and therefore Embodiment 2 is the most economical process.

Note that when the number of reaction regions is 3 or more, ACH may be dividedly supplied to the last reaction region as explained above, but it is preferred not to dividedly supply ACH to the last reaction region. This is because, when the number of reaction regions is 3 or more, a more efficient process can be obtained when dividedly supplying the entire ACH is finished at the reaction region that is next to the last reaction region, the reaction is performed so that the ACH concentration in the liquid at the inlet of the last reaction region becomes about 5% by weight, and the remaining ACH in an amount of about 5% by weight is converted into HBD as much as possible in the last reaction region. Further, in Embodiment 1 and Embodiment 2, an embodiment in which a reaction region is provided in the middle of a circulation line for cyclically supplying the reaction liquid is also included.

In the HBD production of the present invention, in all the reaction regions in the reaction apparatus, hydration of ACH is preferably performed in the presence of an oxidizing agent in order to prevent the catalyst composed mainly of manganese oxide from being reduced and deactivated. As a method for supplying the oxidizing agent for this purpose, since the oxidizing agent is passed through the reaction apparatus together with the liquid, it is usually sufficient when the oxidizing agent is supplied to at least one reaction region in the reaction apparatus. For example, when the oxidizing agent is supplied to the first reaction region, the oxidizing agent is passed through the second reaction region or later, and therefore, the oxidizing agent may be supplied to the first reaction region. However, since the oxidizing agent is gradually consumed in the respective reaction regions, it is particularly preferred to supply the oxidizing agent also to the second reaction region or later depending on the oxidizing agent concentration in the respective reaction regions. Specifically, in the HBD production of the present invention, it is particularly preferred to supply the oxidizing agent to the first reaction region and at least one reaction region other than the first reaction region. Obviously, the oxidizing agent may be supplied to all the reaction regions.

Examples of the oxidizing agent which can be used in the HBD production of the present invention include: gases containing an oxygen atom such as oxygen and ozone; peroxides such as hydrogen peroxide, sodium peroxide, magnesium peroxide, benzoyl peroxide and diacetyl peroxide; peracids and persalts such as performic acid, peracetic acid and ammonium persulfate; or oxyacids and oxoates such as periodic acid, perchloric acid, sodium periodate, iodic acid, bromic acid, potassium chlorate and sodium hypochlorite. Among them, gases containing an oxygen atom such as oxygen and ozone are preferred, and oxygen is particularly preferred. These oxidizing agents may be used solely, or two or more of them may be used in combination. Further, these oxidizing agents may be dissolved in the raw material or diluent to be supplied to the reaction regions, or may be supplied to the reaction regions in the form of gas.

When represented by the molar ratio relative to the raw material ACH, the supply amount of these oxidizing agents is preferably 0.001 to 0.15, and particularly preferably 0.005 to 0.05.

When oxygen is used as the oxidizing agent, pure oxygen may be used, but usually, oxygen is used with dilution with an inert gas such as nitrogen and rare gas. It is also possible to use air directly or to mix air with oxygen or an inert gas to adjust the concentration for use. The oxygen concentration in such an oxygen-containing gas is not particularly limited, but it is preferably 2 to 50% by volume, and particularly preferably 5 to 10% by volume.

When the oxygen-containing gas is used as the oxidizing agent, it is preferred to use a so-called trickle-bed reactor, in which a catalyst is filled as a fixed bed and a reaction liquid flows between a solid phase and a gas phase. By using this, it is possible to carry out good dispersion of the reaction liquid and gas and contact between the reaction liquid and the catalyst. Such a reaction method is called "trickle flow-type continuous reaction". The flows of the reaction liquid and gas may be either countercurrent flow or co-current flow.

When the oxygen-containing gas is used as the oxidizing agent, since it may be supplied from the inlet of the first reaction region in the case of co-current flow, and from the outlet of the last reaction region in the case of countercurrent flow, for the gas to be run through all the reaction regions, the oxygen-containing gas is preferably supplied to the first or last reaction region. However, since oxygen is gradually consumed in the respective reaction regions, it is more preferred to supply the oxygen-containing gas also to reaction regions other than the first or last reaction region depending on the oxygen concentration in the respective reaction regions. In this case, it is particularly preferred to exchange gas in the respective reaction regions by supplying gas having a sufficient oxygen concentration while withdrawing gas whose oxygen concentration has decreased. In this regard, the oxygen concentration of the gas whose oxygen concentration has decreased is not particularly limited. For example, when using a gas containing oxygen at a concentration of 10%, it may be newly supplied while withdrawing a gas whose oxygen concentration has decreased to about 5%. The speed for exchanging gas can be suitably determined depending on the oxygen concentration in the respective reaction regions.

Specifically, when the oxygen-containing gas is run through by co-current flow, it is preferred to supply a gas having a sufficient oxygen concentration and withdraw a gas whose oxygen concentration has decreased in the first reaction region and at least one reaction region other than the first reaction region. Obviously, supplying the gas having a sufficient oxygen concentration and withdrawing the gas whose oxygen concentration has decreased may be carried out in all the reaction regions. Meanwhile, when the oxygen-containing gas is run through by countercurrent flow, it is preferred to supply the gas having a sufficient oxygen concentration and withdraw the gas whose oxygen concentration has decreased in the last reaction region and at least one reaction region other than the last reaction region. Obviously, supplying the gas having a sufficient oxygen concentration and withdrawing the gas whose oxygen concentration has decreased may be carried out in all the reaction regions.

The ratio of the gas which is withdrawn from the reaction regions because of the reduction of the oxygen concentration is not particularly limited. It is possible to withdraw the total amount of the gas to the outside of the system, followed by supply of a new gas having a sufficient oxygen content from a gas withdrawing point or the neighborhood thereof. It is also possible to withdraw only a portion of the gas passed through the catalyst region.

As the catalyst composed mainly of manganese oxide to be used in the HBD production of the present invention, manganese dioxide can be used. In general, manganese dioxide is a manganese oxide having a composition formula of $MnO_{1.7}$ to $MnO_2$, and various crystal structures thereof such as α-type, β-type, γ-type, δ-type and ε-type are known. Further, manganese dioxides in which an alkali metal element is included in a crystal structure (hereinafter referred to as "modified manganese dioxides") are also known, and various crystal structures such as α-type and δ-type of modified manganese dioxides are known. In the present invention, these manganese dioxides can be suitably used, but modified manganese dioxides are more preferred, and modified manganese dioxides having an α-type structure are particularly preferred. The type of the alkali metal element included in modified manganese dioxides is not particularly limited, but lithium, sodium and potassium are preferred. The amount of the alkali metal element included in modified manganese dioxides is not particularly limited, but when represented by the atomic ratio of the alkali metal element relative to the manganese element, alkali metal element/manganese is preferably 0.005 to 0.5, and particularly preferably 0.01 to 0.25.

Manganese dioxide naturally occurs, but when used as a catalyst, it is appropriate to use a manganese dioxide obtained by using a method in which a divalent manganese is oxidized to prepare manganese dioxide, or a method in which a heptavalent manganese is reduced to prepare manganese dioxide, or combination of these methods. Examples of such methods for producing manganese dioxide include a method in which a permanganate compound is reduced in a neutral or alkaline region at 20 to 100° C. (Zeit. Anorg. Allg. Chem., 309, pp. 1-32 and 121-150, (1961)), a method in which an aqueous solution of potassium permanganate is reacted with an aqueous solution of manganese sulfate under acidic conditions (J. Chem. Soc., p. 2189, (1953); Japanese Laid-Open Patent Publication No. S51-71299), a method in which a permanganate is reduced with a hydrohalogenic acid (Japanese Laid-Open Patent Publication No. S63-57535), a method in which a permanganate is reduced with a polyvalent carboxylic acid or polyhydric alcohol (Japanese Laid-Open Patent Publication No. H09-24275, Japanese Laid-Open Patent Publication No. H09-19637), a method in which a permanganate is reduced with hydrazine, hydroxycarboxylic acid or a salt thereof (Japanese Laid-Open Patent Publication No. H06-269666) and a method in which an aqueous solution of manganese sulfate is subjected to electrolytic oxidation.

As the method for preparing the catalyst composed mainly of manganese oxide in the present invention, the aforementioned various methods can be used, but it is preferred to use a method in which a divalent manganese compound and a heptavalent manganese compound are simultaneously used from the viewpoint that the crystal form and specific surface area of the modified manganese dioxide and the type and amount of the alkali metal element can be controlled thereby. As the divalent manganese source to be used for preparing the catalyst, water-soluble compounds such as sulfates, nitrates and halides are preferred, and among them, sulfates are particularly preferred. Meanwhile, as the heptavalent manganese source, permanganates of alkali metal elements are preferred, and among them, lithium permanganate, sodium permanganate and potassium permanganate are particularly preferred. As the alkali metal source, water-soluble compounds such as sulfates, nitrates, bicarbonates and hydroxides can be used, but usually, it is particularly preferred to use the aforementioned permanganates as the alkali metal source. Regarding liquid properties, the modified manganese dioxide can be prepared either under acidic conditions or under basic conditions, but the preparation under acidic conditions is particularly preferred. In the case of the preparation under basic conditions, it is preferred to wash the modified manganese dioxide with an acidic solution such as dilute sulfuric acid before the reaction.

As the catalyst composed mainly of manganese oxide in the present invention, it is also possible to use manganese dioxides containing at least one element selected from among elements other than manganese and alkali metal elements, for example, elements in Groups 2, 3, 4, 5, 6, 8, 9, 10, 11, 12, 13, 14 and 15 of the periodic table. Among them, manganese dioxides containing at least one element selected from alkali earth metals, Sc, Y, Zr, V, Nb, Ta, Cr, Mo, W, Zn, Ga, In, Ge, Sn, Pb and Bi are preferred because these are excellent in reaction activity of ACH hydration and selectivity of HBD. Particularly preferred are manganese dioxides containing at least one element selected from V, Sn and Bi because these are particularly excellent in reaction activity of ACH hydration and selectivity of HBD. It is also possible to suitably use manganese dioxides containing two or more elements.

As the method for adding these elements to manganese dioxide, any method such as impregnation, adsorption, kneading and coprecipitation may be used. As the element source, water-soluble compounds such as nitrates and sulfates, and oxides, hydroxides, etc. can be used. For example, when preparing a vanadium-containing manganese oxide catalyst, as the vanadium source, water-soluble salts such as vanadium sulfate and vanadium chloride are preferably used, and vanadium sulfate is particularly preferably used. When preparing a tin-containing manganese oxide catalyst, as the tin source, water-soluble salts such as tin sulfate and tin chloride are preferably used, and tin sulfate is particularly preferably used. When preparing a bismuth-containing manganese oxide, as the bismuth source, water-soluble salts such as bismuth sulfate and bismuth nitrate can be used, but bismuth oxide is particularly preferably used.

The amount of these elements contained in manganese dioxide is not particularly limited, but when represented by the atomic ratio relative to manganese element, elements/manganese contained in manganese dioxide is preferably 0.001 to 0.1, and particularly preferably 0.002 to 0.04.

In the present invention, a particularly preferred catalyst composed mainly of manganese oxide comprises a compound represented by composition formula:

$Mn_aK_bM_cO_d$ 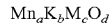

wherein: Mn represents manganese; K represents potassium; O represents oxygen; M represents at least one element selected from V, Sn and Bi; and regarding the atomic ratio of each element, when a=1, b is 0.005 to 0.5, c is 0.001 to 0.1, and d is 1.7 to 2.0. Further, in addition to the above-described compound, hydrated water may also be contained in the catalyst composed mainly of manganese oxide.

In the HBD production of the present invention, the manganese oxide prepared according to the above-described method can be molded into a form of pellet or tablet to be used as a fixed bed catalyst or molded into a form of granule or microsphere to be used as a slurry bed catalyst, and can be filled or dispersed in the reaction regions to be used for hydration of ACH. Further, a molded product obtained by using a compound having plasticity and bonding capability such as silica and clay mineral can also be used.

The method for producing the raw material ACH which can be used for the HBD production of the present invention is not particularly limited. For example, it is possible to use the ACH which is synthesized from acetone and hydrocyanic acid obtained by dehydration reaction of formamide. Further, it is also possible to use the ACH which is synthesized from acetone and hydrocyanic acid obtained by a reaction between methane and ammonia as in the case of the Andrussow oxidation or the BMA process, the ACH which is synthesized from acetone and hydrocyanic acid obtained by ammoxidation of propane, or the like. In general, synthesis of ACH by means of a reaction between hydrocyanic acid and acetone is quantitatively progressed in the presence of a catalyst such as an alkali metal compound, amine and basic ion exchange resin, and ACH is obtained with a high yield. In the HBD production of the present invention, it is possible to use ACH synthesized with using these catalysts. In this case, ACH can be used after subjected to distillation and purification, and can also be used without distillation and purification.

In the present invention, the reaction temperature of hydration of ACH is preferably 20 to 120° C., and particularly preferably 30 to 90° C. The reaction pressure may be under reduced pressure or under high pressure, but is preferably 0.01 to 1.0 MPa, and particularly preferably 0.05 to 0.5 MPa. As the ACH retention time in each reaction region, an optimum value is selected depending on the reaction method and catalyst activity, but usually, it is preferably 30 seconds to 15 hours, more preferably 15 minutes to 10 hours, and particularly preferably 30 minutes to 5 hours.

In the HBD production of the present invention, pH of the reaction region supply liquid (C) supplied to the reaction regions is preferably adjusted to 4 or more, and particularly preferably adjusted to 4 to 8. The adjustment of pH can be carried out by cyclically supplying the reaction liquid as explained above, and in addition, amines disclosed in Japanese Laid-Open Patent Publication No. H11-335341 and oxides and hydroxides of alkali metals disclosed in Japanese Laid-Open Patent Publication No. H02-193952 can be used.

The reaction apparatus for the HBD production of the present invention is a reaction apparatus for producing α-hydroxyisobutyric acid amide by hydration of acetone cyanohydrin in the presence of a catalyst composed mainly of manganese oxide, wherein the reaction apparatus has at least two reaction regions connected in series and further has:

(a) a piping for supplying a reaction raw material liquid containing the acetone cyanohydrin dividedly to a first reaction region (I) and at least one reaction region other than the first reaction region in the reaction apparatus; and/or (b) a piping for cyclically supplying at least a portion of a reaction liquid withdrawn from at least one reaction region to the first reaction region (I) in the reaction apparatus, and wherein the reaction apparatus further has a piping for supplying an oxidizing agent to at least one reaction region.

The reaction apparatus for the HBD production of the present invention preferably has a piping for cyclically supplying a portion of the reaction liquid withdrawn from at least one reaction region to at least one reaction region other than the first reaction region. In this case, the embodiment of the piping for cyclically supplying the reaction liquid withdrawn from the aforementioned reaction region to the reaction region is not particularly limited. For example, it is possible to employ an embodiment in which the piping for cyclically supplying the reaction liquid withdrawn from the reaction region is independently connected to the reaction region, or an embodiment in which the reaction liquid is mixed with the reaction raw material liquid and the diluent such as water, acetone and HBD in a raw material preparation tank, storage tank or the like before being supplied to the reaction region and these materials are simultaneously supplied to the reaction region with one piping, or an embodiment in which the piping for cyclically supplying the reaction liquid withdrawn from the reaction region is connected to a piping for supplying the reaction raw material liquid and the diluent such as water, acetone and HBD to the reaction region or a piping for connecting reaction regions. Further, it is also possible to provide the reaction region in the middle of the circulation line for cyclically supplying the reaction liquid. Moreover, the reaction apparatus may have at least one circulation loop composed of: at least one reaction region (II) other than the first reaction region; at least one reaction region (IV) from which the reaction liquid is withdrawn in order to cyclically supply the reaction liquid to the reaction region; and a piping for connecting the former reaction region and the latter reaction region, and it is more preferred that both the reaction region (II) and the reaction region (IV), which constitute at least one circulation loop (V) among said circulation loop, are placed at a position nearer to the outlet of the reaction apparatus of the present invention (downstream) compared to a reaction region that is nearest to the inlet of the reaction apparatus among the at least one reaction region from which the reaction liquid is withdrawn in order to cyclically supply the reaction liquid to the first reaction region (I). Alternatively, when the reaction liquid is withdrawn from a plurality of reaction regions in order to cyclically supply the reaction liquid to the reaction region (I), it is even more preferred that both the reaction region (II) and the reaction region (IV), which constitute at least one circulation loop (V) among said circulation loop, are provided at a position nearer to the outlet of the reaction apparatus (downstream) compared to a reaction region in which the integrated quantity of the reaction liquid withdrawn from the respective reaction regions exceeds 50% of the total amount of the reaction liquid cyclically supplied to the reaction region (I) for the first time, and it is most preferred that both the reaction region (II) and the reaction region (IV), which constitute at least one circulation loop (V) among said circulation loop, are provided at a position nearer to the outlet of the reaction apparatus (downstream) compared to all the reaction regions from which the reaction liquid is withdrawn in order to cyclically supply the reaction liquid to the first reaction region (I).

Regarding the arrangement of the reaction region (II) and the reaction region (IV) which constitute the circulation loop (V), it is preferred that the reaction region (IV) is provided at a position nearer to the outlet of the reaction apparatus of the present invention compared to the reaction region (II). Alternatively, it is preferred that the reaction region (II) is identical to the reaction region (IV).

The reaction apparatus for the HBD production of the present invention preferably has a piping for supplying a diluent containing at least one compound selected from water, acetone, HBD and formamide to at least one reaction region. The reaction apparatus more preferably has a piping for supplying the diluent to the reaction region to which ACH is dividedly supplied. In this case, the embodiment of the piping for supplying the diluent to the reaction region is not particularly limited. For example, it is possible to employ an embodiment in which the piping for supplying the diluent is independently connected to the reaction region, or an embodiment in which the diluent is mixed with the reaction raw material liquid in a raw material preparation tank before being supplied to the reaction region and these materials are simultaneously supplied to the reaction region with one piping, or an embodiment in which the piping for supplying the diluent is connected to the piping for supplying the reaction raw material liquid to the reaction region.

The reaction apparatus for the HBD production of the present invention has a piping for supplying an oxidizing agent to at least one reaction region. In this case, the embodiment of the piping for supplying the oxidizing agent to the reaction region is not particularly limited.

In the reaction apparatus for the HBD production of the present invention, it is preferred that an equipment for withdrawing the oxidizing agent is connected to the first reaction region (I) and/or a position between at least one reaction region other than the first reaction region and another reaction region, or the the first reaction region (I) and/or the middle portion of at least one reaction region other than the first reaction region.

<Specific Examples of Reaction Apparatus and Production Method for Carrying out the Present Invention>

Hereinafter, specific examples of a preferred reaction apparatus and production method for carrying out the present invention (combination method) will be described. FIG. 1 is a process flow diagram showing an example of a reaction apparatus for the HBD production composed of three reactors, i.e., a first reactor $1a$, a second reactor $1b$ and a third reactor $1c$.

To the first reactor $1a$, the second reactor $1b$ and the third reactor $1c$, a first reaction region $2a$, a second reaction region $2b$ and a third reaction region $2c$, in each of which a catalyst is filled, are provided respectively. To the first reactor $1a$, a supply line $10a$ of reaction liquid to be supplied to the inlet of the first reaction region and an oxidizing agent supply line $4a$ are connected, and to the opposite side across the first reaction region $2a$, an outflow line $11a$ of reaction liquid flowing out from the outlet of the first reaction region and an oxidizing agent withdrawing line $5a$ are connected. To the second reactor $1b$, a supply line $10b$ of reaction liquid to be supplied to the inlet of the second reaction region and an oxidizing agent supply line $4b$ are connected, and to the opposite side across the second reaction region $2b$, an outflow line $11b$ of reaction liquid flowing out from the outlet of the second reaction region and an oxidizing agent withdrawing line $5b$ are connected. To the third reactor $1c$, a supply line $10c$ of reaction liquid to be supplied to the inlet of the third reaction region and an oxidizing agent supply line $4c$ are connected, and to the opposite side across the third reaction region $2c$, an outflow line $11c$ of reaction liquid flowing out from the outlet of the third reaction region and an oxidizing agent withdrawing line $5c$ are connected.

$3a$ and $3b$ are a supply line of reaction raw material liquid containing ACH. $6a$ and $6b$ are a circulation line for returning the reaction liquid from the outlet of the reaction region to the inlet of the original reaction region. $7$ is a cooler for cooling the reaction liquid circulated from the outlet of the reaction region. $8$ is a pump for delivering the reaction liquid from the outlet of the reaction region. $9$ is a heater for heating the reaction raw material liquid to a predetermined temperature. $12a$ and $12b$ are liquid reservoirs for temporarily storing the reaction liquid from the outlet of the reaction region.

An example of the method for producing HBD using the reaction apparatus in FIG. 1 will be described. The reaction raw material liquid containing ACH is dividedly supplied from the reaction raw material liquid supply lines 3a and 3b via the heaters 9. From 3a, a mixed raw material obtained by adding at least acetone to a mixture of ACH and water is supplied as the reaction raw material liquid. Meanwhile, from 3b, ACH alone as a raw material, or a mixed raw material obtained by adding at least water and/or acetone to ACH is supplied as the reaction raw material liquid. Note that in FIG. 1, reaction raw materials consisting of ACH, water, acetone, etc. are mixed together and then the mixture is supplied to the reactors using 3a and 3b, but these components may also be respectively supplied to the reactors using independent supply lines.

The ACH concentration and the water concentration in the reaction raw material liquid supplied from 3a are not particularly limited, but from a practical viewpoint, it is preferred that the ACH concentration is 30 to 60% by weight and that the water concentration is 70 to 40% by weight, and it is particularly preferred that the ACH concentration is 35 to 50% by weight and that the water concentration is 65 to 50% by weight. Further, the acetone concentration in the reaction raw material liquid is not particularly limited, but it is preferably 3 to 20% by weight, and more preferably 5 to 15% by weight. Meanwhile, the ACH concentration and the water concentration in the reaction raw material liquid supplied from 3b are not particularly limited, and it is preferred that the ACH concentration is 30 to 100% by weight and that the water concentration is 0 to 50% by weight. Further, the acetone concentration in the reaction raw material liquid is preferably 0 to 20% by weight.

The reaction raw material liquid containing ACH supplied from 3a and 3b is mixed with the reaction liquid from the outlet of the reaction region circulated from 6a and 6b, and the mixture is supplied to the respective reactors via 10a and 10b. As previously described, the ratio of the supply rate of the reaction liquid from the outlet of the reaction region circulated from 6a and 6b (X) to the difference between the supply rate of the whole reaction liquid supplied to the reaction regions 2a and 2b (Y) and the supply rate of the reaction liquid cyclically supplied from 6a and 6b (X) ((X)/((Y)−(X))), i.e., the circulation ratio is not particularly limited, but when represented by the volume velocity ratio, it is preferably 0.5 to 50, and particularly preferably 1 to 20. Note that in FIG. 1, the reaction raw material liquid is mixed with the reaction liquid from the outlet of the reaction region and then the mixture is supplied to the reactors via 10a and 10b, but these liquids may also be respectively supplied to the reactors using independent supply lines.

Hydration of ACH is performed with the previously described reaction temperature and reaction pressure. The method for controlling the reaction temperature of hydration of ACH is not particularly limited. For example, it is possible to use: a method in which a heating medium or a hot-water-circulated jacket is provided around the reaction region filled with the catalyst; a method in which a heat transfer coil is provided to the inside of the reaction region; and a method in which the heat-retention means for preventing heat dissipation is provided to the outside of the reaction region and the heater 9 or cooler 7 is provided to the lines for flow of the reaction raw material liquid and the reaction liquid from the outlet of the reaction region (3a, 6a, 13a, 3b, 6b and 13b in FIG. 1) to adjust the temperature of the reaction liquid. Note that FIG. 1 shows an example in which the heater 9 and the cooler 7 are provided, but it is not required to provide the heater 9 and the cooler 7 when the liquid temperature of the mixture of the reaction raw material liquid and the reaction liquid from the outlet of the reaction region can be controlled to a predetermined temperature for performing hydration of ACH without use of the heater 9 and the cooler 7. From a practical viewpoint, it is preferred to provide the heater 9 and the cooler 7 to control the reaction temperature because it becomes easier to operate the reaction apparatus stably.

As previously described, in order to prevent the catalyst composed mainly of manganese oxide from being reduced and deactivated, an oxidizing agent is supplied from the oxidizing agent supply lines 4a, 4b and 4c. When using an oxygen-containing gas as the oxidizing agent, the oxygen-containing gas is supplied from the oxidizing agent supply lines 4a, 4b and 4c, and the gas whose oxygen concentration has decreased is withdrawn from the oxidizing agent withdrawing lines 5a, 5b and 5c. As the gas to be supplied from 4a, 4b and 4c, a fresh oxygen-containing gas may be used, or a gas obtained by mixing the gas whose oxygen concentration has decreased withdrawn from 5a, 5b and 5c with a fresh oxygen-containing gas to provide a sufficient oxygen concentration may be used. When the gas withdrawn from 5a, 5b and 5c still has a sufficient oxygen concentration, it may be directly supplied to the original reaction region or other reaction regions via 4a, 4b and 4c.

A portion of ACH supplied from the reaction liquid supply line 10a becomes HBD by hydration in the first reaction region 2a. The reaction liquid from the outlet of the reaction region flowing out from the first reaction region 2a is passed through the outflow line 11a and temporarily stored in the liquid reservoir 12a. After that, it is dividedly supplied to 6a as a circulation liquid to the first reaction region and to 13a as a supply liquid to the second reaction region at a predetermined ratio. Usually, the supply rate of the liquid to the second reaction region is the same as the supply rate of the reaction raw material liquid supplied from 3a.

The supply liquid to the second reaction region delivered from 13a is joined together with the reaction raw material liquid supplied from 3b and the circulation liquid from the outlet of the second reaction region delivered from 6b, and the mixture is supplied to the second reaction region 2b via the reaction liquid supply line 10b. In the second reaction region, ACH supplied from 3b and ACH circulated from 6b are converted into HBD, and therefore, the HBD concentration in the reaction liquid from the outlet of the second reaction region is higher than the HBD concentration in the reaction liquid from the outlet of the first reaction region. The reaction liquid from the outlet of the reaction region flowing out from the second reaction region 2b is passed through the outflow line 11b and temporarily stored in the liquid reservoir 12b. After that, it is dividedly supplied to 6b as a circulation liquid to the second reaction region and to 13b as a supply liquid to the third reaction region at a predetermined ratio. Usually, the supply rate of the liquid to the third reaction region is the same as the sum of the supply rate of the reaction raw material liquid supplied from 3b and the supply rate of the liquid to the second reaction region supplied from 13a.

The supply liquid to the third reaction region delivered from 13b is supplied to the third reaction region 2c via 10c. In the third reaction region 2c, a major part of ACH in the reaction liquid is converted into HBD, and finally, a solution of HBD having a concentration of 40% by weight or more is obtained and is delivered from 11c to an apparatus for the next process or a storage apparatus.

The process flow diagram of the preferred reaction apparatus for carrying out the present invention is not limited to FIG. 1. For example, there are various methods such as: a method in which a plurality of reaction regions are provided in one reactor and a reaction liquid circulation line is provided to each of them (FIG. 2); a method in which the reaction liquid is withdrawn from the middle of one reaction region, the liquid temperature is adjusted using a heat exchanger and then the liquid is returned to the reaction region (FIG. 3); and a method in which the circulation liquid is returned to a plurality of areas in one reaction region (FIG. 4).

EXAMPLES

Hereinafter, the present invention will be more specifically described by way of examples and comparative examples. However, the scope of the present invention is not limited by these examples.
Preparation of Catalyst To a solution obtained by dissolving 62.92 g (0.398 mol) of potassium permanganate in 220 ml of water, a solution obtained by dissolving 54.43 g (0.322 mol) of manganese sulfate monohydrate in 215 ml of water and further mixing it with 99.54 g (0.964 mol) of concentrated sulfuric acid was added by pouring rapidly with stirring at 75° C. The mixture was continuously stirred at 70° C. for 2 hours and then further stirred at 90° C. for 4 hours to be matured. After that, a solution obtained by suspending 1.90 g (0.007 mol) of bismuth (III) oxide in 440 ml of water was added thereto by pouring rapidly. The mixture was stirred at room temperature for 30 minutes, and then the obtained precipitate was filtered and washed 4 times with 200 ml of water, thereby obtaining a precipitated cake.

The obtained cake was molded using an extruder (cylinder diameter: 35 mmΦ, nozzle diameter: 1.5 mmΦ×24 holes, rate of hole area: 4.4%, oil pressure type), and it was dried at 110° C. for 15 hours using a ventilation dryer, thereby obtaining about 60 g of a pellet-type molded catalyst having a diameter of about 1 mmϕ and a length of 5 to 10 mm. The content of metal components of the obtained catalyst was measured, and in each case, bismuth/potassium/manganese was 0.01/0.09/1.0 (atomic ratio).
Hydration of ACH

Example 1

Hydration of ACH was performed using a reaction apparatus shown in FIGS. 5. 1a, 1b and 1c are a reactor made of glass having an inner diameter of about 18 mmϕ equipped with a jacket (a first reactor, a second reactor and a third reactor, respectively). 2a is a first reaction region, and it was filled with 16 g of the catalyst prepared according to the above-described method. 2b is a second reaction region, and it was filled with 16 g of the catalyst prepared according to the above-described method. 2c is a third reaction region, and it was filled with 8 g of the catalyst prepared according to the above-described method. 3a is a first reaction raw material liquid supply line, and the first reaction raw material liquid consisting of 55.5% by weight of pure water, 9.5% by weight of acetone and 35% by weight of ACH was supplied at a rate of 14.8 g/hr. 3b is a second reaction raw material liquid supply line, and the second reaction raw material liquid consisting of 17% by weight of pure water, 13% by weight of acetone and 70% by weight of ACH was supplied at a rate of 2.47 g/hr. The ratio of ACH supplied to the first reaction raw material liquid supply line to all the supplied ACH was 75% by weight. 4a is a first oxidizing agent supply line, and an oxygen-containing gas consisting of 9% oxygen and 91% nitrogen on the volume basis was supplied at a rate of 26.7 ml/hr. The oxygen-containing gas supplied from 4a was passed through the first reaction region 2a to be led to the outlet of the first reactor (outflow line) 11a and to a reaction liquid pool (liquid reservoir) 12a at the outlet of the first reaction region, and was completely withdrawn from a first oxidizing agent withdrawing line 5a to the outside of the system. 4b is a second oxidizing agent supply line, and an oxygen-containing gas consisting of 9% oxygen and 91% nitrogen on the volume basis was supplied at a rate of 26.7 ml/hr. The oxygen-containing gas supplied from 4b was passed through the second reaction region 2b, the outlet of the second reactor (outflow line) 11b, a reaction liquid pool (liquid reservoir) 12b at the outlet of the second reaction region and a liquid supply line 10c at the inlet of the third reaction region to be led to the third reactor 1c, and further passed through the third reaction region 2c and then withdrawn from the outlet of the third reactor (outflow line) 11c to the outside of the system together with the reaction liquid at the outlet of the third reaction region. The whole reaction liquid from the outlet of the first reaction region flowing out from the outlet of the first reactor 11a was temporarily collected into the reaction liquid pool 12a at the outlet of the first reaction region. A portion of the collected reaction liquid was delivered to a liquid supply line 10a at the inlet of the first reaction region via a circulation line 6a for the reaction liquid from the outlet of the first reaction region using a liquid delivery pump 8a at a rate of 120 g/hr. The circulation ratio of the reaction liquid circulated to the inlet of the first reaction region was 8.1. The reaction liquid pool 12a at the outlet of the first reaction region is equipped with a liquid level sensor, and the reaction liquid flowing out from the outlet of the first reactor 11a at a rate higher than 120 g/hr was delivered to the second reactor 1b via a liquid delivery line 13a to the second reaction region while controlling the liquid level of the reaction liquid pool 12a at the outlet of the first reaction region to be constant by means of the liquid level sensor and a liquid delivery pump 8t. The supply rate of the liquid delivered from the liquid delivery pump 8t was 14.8 g/hr. 12b is a reaction liquid pool (liquid reservoir) at the outlet of the second reaction region. The whole reaction liquid flowing out from the outlet of the second reactor (outflow line) 11b was temporarily collected into a reaction product liquid pool 12b at the outlet of the second reaction region. A portion of the collected reaction liquid was delivered to a liquid supply line 10b at the inlet of the second reaction region via a circulation line 6b for the reaction liquid from the outlet of the second reaction region using a liquid delivery pump 8b at a rate of 26.5 g/hr. The circulation ratio of the reaction liquid circulated to the inlet of the second reaction region was 1.5. The reaction liquid from the outlet of the second reaction region flowing out from the outlet of the second reactor 11b at a rate higher than 26.5 g/hr was overflowed from an opening provided in the side surface of the reaction liquid pool 12b at the outlet of the second reaction region and delivered to the third reactor 1c via a liquid delivery tube (liquid delivery line) 13b. Note that the oxygen-containing gas supplied from the second oxidizing agent supply line was delivered to the third reactor 1c from the same liquid delivery tube 13b. The reaction liquid from the outlet of the second reaction region delivered to the third reactor 1c was passed through the third reaction region 2c and withdrawn from the outlet of the third reactor 11c to the outside of the system. In each of the reaction regions 2a, 2b and 2c, the reaction liquid ran down on the surface of the catalyst, and in each case, the catalyst layer was held in a state of so-called "trickle bed". The liquid in the reaction liquid pool 12a at the outlet of the first reaction region, the liquid in the reaction liquid pool 12b at the outlet of the second reaction region and the liquid at the outlet of the third reactor 11c were analyzed by HPLC, and the ACH concentration was analyzed. The reaction temperature was suitably adjusted so that the ACH concentration at the outlet of the third reactor 11c did not exceed 1% by weight. The amount of the production of HBD as the target product and time-dependent change in the conversion of ACH as the raw material are shown in Table 1, and the ACH concentration in liquids at inlets and outlets of the reactors 1a, 1b and 1c calculated from analysis values and liquid flow rates is shown in Table 2. Note that at each point, the yield of HBD as the target product at the outlet of the third reactor 11c was 95% or more. Further, the manganese concentration in the liquid in the reaction liquid pool 12a at the outlet of the first reaction region was measured using a polarized Zeeman atomic absorption spectrometer (manufactured by Hitachi High-Technologies, Z-2000). The results are shown in Table 2.

At the point when the reaction temperature for maintaining the ACH concentration at the outlet of the third reactor 11c at 1% or less became 56° C. or higher, the reaction was terminated. The period of the operation was 750 days, and the total amount of the production of HBD was 3717.8 g per 1 g of the catalyst.

TABLE 1

| Time days | HBD production amount g-HBD/g-cat | Reaction temperature ° C. | ACH conversion % | | |
|---|---|---|---|---|---|
| | | | 11a | 11b | 11c |
| 54 | 250.4 | 47.5 | 84.4 | 93.9 | 97.9 |
| 300 | 1432.5 | 48.5 | 82.6 | 94.5 | 98.6 |
| 501 | 2432.2 | 48 | 77.7 | 93.6 | 98.0 |
| 600 | 2912.1 | 49 | 75.2 | 93.1 | 97.7 |
| 750 | 3717.8 | 56 | 74.3 | 92.5 | 97.4 |

TABLE 2

| Time days | ACH concentration % | | | | | | | Mn concentration ppm |
|---|---|---|---|---|---|---|---|---|
| | 3a | 3b | 10a | 10b | 10c | 11a | 11b | 11c | 12a |
| 54 | 35.0 | 70 | 8.5 | 7.2 | 2.4 | 5.3 | 2.4 | 0.8 | 1.1 |
| 300 | 35.0 | 70 | 9.6 | 7.5 | 2.2 | 6.5 | 2.2 | 0.6 | 0.6 |
| 501 | 35.0 | 70 | 11.3 | 8.4 | 2.6 | 8.5 | 2.6 | 0.8 | 0.9 |
| 600 | 35.0 | 70 | 12.4 | 8.9 | 2.8 | 9.7 | 2.8 | 0.9 | 1.9 |
| 750 | 35.0 | 70 | 12.9 | 9.3 | 3.0 | 10.3 | 3.0 | 1.1 | 1.3 |

Example 2

Hydration of ACH was performed under the same reaction conditions as those in Example 1, except that a reaction raw material liquid consisting of 50% by weight of pure water, 10% by weight of acetone and 40% by weight of ACH was supplied from the first reaction raw material liquid supply line 3a at a rate of 17.28 g/hr and no raw material was supplied from the second reaction raw material liquid supply line 3b. The amount of the production of HBD as the target product and time-dependent change in the conversion of ACH as the raw material are shown in Table 3, and the ACH concentration in liquids at inlets and outlets of the reactors 1a, 1b and 1c calculated from analysis values and liquid flow rates is shown in Table 4. Note that at each point, the yield of HBD as the target product at the outlet of the third reactor (outflow line) 11c was 95% or more. Further, the manganese concentration in the liquid in the reaction liquid pool (liquid reservoir) 12a at the outlet of the first reaction region was measured using a polarized Zeeman atomic absorption spectrometer (manufactured by Hitachi High-Technologies, Z-2000). The results are shown in Table 4. The Mn concentration in the reaction liquid at the outlet of the first reaction region was 1.8 to 2.0 ppm.

On day 102 of the reaction, the reaction temperature required for maintaining the ACH concentration at the outlet of the third reactor 11c at 1% or less was 47.5° C., and at that point, the total amount of the production of HBD was 483.8 g per 1 g of the catalyst.

TABLE 3

| Time days | HBD production amount g-HBD/g-cat | Reaction temperature ° C. | ACH conversion % | | |
|---|---|---|---|---|---|
| | | | 11a | 11b | 11c |
| 55 | 259.5 | 47.0 | 75.5 | 94.5 | 98.4 |
| 102 | 483.8 | 47.5 | 74.4 | 94.7 | 98.2 |

TABLE 4

| Time days | ACH concentration % | | | | | | | Mn concentration ppm |
|---|---|---|---|---|---|---|---|---|
| | 3a | 10a | 10b | 10c | 11a | 11b | 11c | 12a |
| 55 | 40.0 | 13.6 | 5.2 | 2.2 | 9.8 | 2.2 | 0.6 | 2.0 |
| 102 | 40.0 | 14.0 | 5.3 | 2.1 | 10.3 | 2.1 | 0.7 | 1.8 |

Example 3

Hydration of acetone cyanohydrin was performed using a reaction apparatus shown in FIG. 6. 1a, 1b and 1c are a reactor made of glass having an inner diameter of about 18 mmφ equipped with a jacket (a first reactor, a second reactor and a third reactor, respectively). 2a is a first reaction region, and it was filled with 8 g of the catalyst prepared according to the above-described method. 2b is a second reaction region, and it was filled with 8 g of the catalyst prepared according to the above-described method. 2c is a third reaction region, and it was filled with 8 g of the catalyst prepared according to the above-described method. 3a is a raw material supply tube (supply line), and the first raw material consisting of 50.0% by weight of pure water, 10.0% by weight of acetone and 40% by weight of acetone cyanohydrin (referred to as ACH in Tables) was supplied at a rate of 12.0 g/hr. 4a is an oxidizing agent supply tube (supply line), and as the oxygen-containing gas, air was supplied at a rate of 16.0 ml/hr. The oxygen-containing gas supplied from 4a was passed through the first reaction region 2a and further passed through the outlet of the reactor (outflow line) 11a, a first reaction liquid pool (liquid reservoir) 12a, a liquid delivery tube (liquid delivery line) 13a, the second reactor 1b, the second reaction region 2b, the outlet of the reactor (outflow line) 11b, a second reaction liquid pool (liquid reservoir) 12b, a liquid delivery tube (liquid delivery line) 13b, the third reactor 1c and the third reaction region 2c, and discharged together with the reaction liquid from the outlet of the reactor (outflow line) 11c to the outside of the system. 12a is the first reaction liquid pool. The whole reaction liquid flowing out from the first reactor 1a was temporarily collected into the first reaction liquid pool 12a and delivered to a reaction liquid supply tube (supply line) 10a via a reaction liquid circulation line 6a using a liquid delivery pump 8a at a rate of 120 g/hr. The reaction liquid flowing out from the first reactor 1a at a rate higher than 120 g/hr was overflowed from an opening provided in the side surface of the first reaction liquid pool 12a and delivered to the second reactor 1b via a liquid delivery tube 13a. The reaction liquid delivered from a reaction liquid supply tube 10b to the second reactor 1b was passed through the second reaction region 2b and delivered from the outlet of the reactor 11b to the second liquid pool 12b to be temporarily collected. The reaction liquid was delivered from the second liquid pool 12b to a reaction liquid supply tube 10b via a reaction liquid circulation line 6b using a liquid delivery pump 8b at a rate of 120 g/hr. The reaction liquid flowing out from the second reactor 1b at a rate higher than 120 g/hr was overflowed from an opening provided in the side surface of the second reaction liquid pool 12b and delivered to the third reactor 1c via a liquid delivery tube 13b. The reaction liquid delivered to the third reactor 1c was passed through the third reaction region 2c and discharged from the outlet of the third reactor 11c to the outside of the system. In each of the reaction regions 2a, 2b and 2c, the reaction liquid ran down on the surface of the catalyst, and in each case, the catalyst layer was held in a state of so-called "trickle bed". The reaction liquid in the first reaction liquid pool 12a, the reaction liquid in the second reaction liquid pool 12b and the reaction liquid at the outlet of the third reactor 11c were analyzed by HPLC, and the acetone cyanohydrin concentration was analyzed. The reaction temperature was suitably adjusted so that the acetone cyanohydrin concentration at the outlet of the third reactor 11c did not exceed 1% by weight. The amount of the production of α-hydroxyisobutyric acid amide (HBD) as the target product and time-dependent change in the conversion of acetone cyanohydrin as the raw material are shown in Table 5, and the acetone cyanohydrin concentration in reaction liquids at the inlets and outlets of the reactors 1a, 1b and 1c calculated from analysis values and reaction liquid flow rates is shown in Table 6. Note that at each point, the yield of α-hydroxyisobutyric acid amide as the target product at the outlet of the third reactor 11c was 95% or more. Further, the manganese concentration in the reaction liquid in the first reaction liquid pool 12a was measured using an atomic absorption spectrometer (manufactured by Hitachi High-Technologies, Z-2000). The results are shown in Table 6.

At the point when the reaction temperature for maintaining the acetone cyanohydrin concentration at the outlet of the third reactor 11c at 1% or less became 56° C. or higher, the reaction was terminated. The total amount of the production of α-hydroxyisobutyric acid amide was 2261.5 g per 1 g of the catalyst.

TABLE 5

| Time days | HBD production amount g-HBD/g-cat | Reaction temperature ° C. | ACH conversion % | | |
|---|---|---|---|---|---|
| | | | 11a | 11b | 11c |
| 50 | 278.3 | 49.0 | 69.2 | 90.0 | 97.8 |
| 152 | 844.9 | 50.5 | 63.7 | 88.5 | 97.8 |

TABLE 5-continued

| Time days | HBD production amount g-HBD/g-cat | Reaction temperature ° C. | ACH conversion % | | |
|---|---|---|---|---|---|
| | | | 11a | 11b | 11c |
| 301 | 1679.7 | 50.5 | 64.6 | 90.3 | 98.1 |
| 405 | 2261.5 | 56.0 | 56.6 | 82.7 | 97.6 |

TABLE 6

| Time days | ACH concentration % | | | | | | | Mn concentration ppm |
|---|---|---|---|---|---|---|---|---|
| | 3a | 10a | 10b | 10c | 11a | 11b | 11c | 12a |
| 50 | 40.0 | 14.9 | 4.8 | 4.0 | 12.3 | 4.0 | 0.9 | 3.6 |
| 152 | 40.0 | 16.9 | 5.5 | 4.6 | 14.5 | 4.6 | 0.9 | 2.7 |
| 301 | 40.0 | 16.5 | 4.8 | 3.9 | 14.2 | 3.9 | 0.8 | 2.0 |
| 405 | 40.0 | 19.4 | 7.9 | 6.9 | 17.4 | 6.9 | 1.0 | 4.5 |

The present invention also includes the following embodiments:

<1> A method for producing α-hydroxyisobutyric acid amide by hydration of acetone cyanohydrin in the presence of a catalyst composed mainly of manganese oxide using a reaction apparatus in which at least two reaction regions are connected in series, wherein the method comprises at least one step selected from:

a step (A) of supplying a reaction raw material liquid containing acetone cyanohydrin to the first reaction region (I) and at least one reaction region (II) other than the first reaction region in the reaction apparatus; and a step (B) of cyclically supplying at least a portion of a reaction liquid withdrawn from at least one reaction region (III) to the first reaction region (I) in the reaction apparatus.

<2> The method for producing α-hydroxyisobutyric acid amide according to item <1>, wherein the number of the reaction regions connected in series is 7 or less.

<3> The method for producing α-hydroxyisobutyric acid amide according to item <1> or <2>, wherein the number of the reaction regions to which the reaction raw material liquid containing acetone cyanohydrin is supplied in the step (A) is 5 or less.

<4> The method for producing α-hydroxyisobutyric acid amide according to any one of items <1> to <3>, wherein the molar ratio between water and acetone cyanohydrin in a reaction region supply liquid (C) supplied to the reaction regions is such that the amount of water is 1 to 200 mol relative to 1 mol of acetone cyanohydrin.

<5> The method for producing α-hydroxyisobutyric acid amide according to item <4>, wherein acetone is contained in the reaction region supply liquid (C).

<6> The method for producing α-hydroxyisobutyric acid amide according to item <4> or <5>, wherein α-hydroxyisobutyric acid amide is contained in the reaction region supply liquid (C).

<7> The method for producing α-hydroxyisobutyric acid amide according to any one of items <1> to <6>, wherein the ratio of the acetone cyanohydrin in the total amount of the reaction region supply liquid (C) is 25% by weight or less.

<8> The method for producing α-hydroxyisobutyric acid amide according to any one of items <1> to <7>, wherein the acetone cyanohydrin concentration in the reaction raw material liquid is 30% by weight or more.

<9> The method for producing α-hydroxyisobutyric acid amide according to any one of items <1> to <8>, wherein in the step (B), at least a portion of the reaction liquid withdrawn from the at least one reaction region (III) is further cyclically supplied to the at least one reaction region (II) other than the first reaction region.

<10> The method for producing α-hydroxyisobutyric acid amide according to any one of items <1> to <9>, wherein an oxidizing agent is supplied to the at least one reaction region (III) in the reaction apparatus.

<11> The method for producing α-hydroxyisobutyric acid amide according to any one of items <1> to <10>, wherein the oxidizing agent is supplied to all the reaction regions in the reaction apparatus.

<12> The method for producing α-hydroxyisobutyric acid amide according to item <10> or <11>, wherein an oxygen atom-containing gas is used as the oxidizing agent.

<13> The method for producing α-hydroxyisobutyric acid amide according to item <10> or <11>, wherein an oxygen-containing gas is used as the oxidizing agent, and wherein the oxygen concentration in the oxygen-containing gas is 2 to 50% by volume.

<14> The method for producing α-hydroxyisobutyric acid amide according to item <13>, wherein the gas in the reaction region is exchanged by supplying a gas having a sufficient oxygen concentration while withdrawing a gas having a reduced oxygen concentration.

<15> The method for producing α-hydroxyisobutyric acid amide according to any one of items <12> to <14>, wherein a reaction method is a trickle flow-type continuous reaction method.

<16> The method for producing α-hydroxyisobutyric acid amide according to any one of items <1> to <15>, wherein the catalyst composed mainly of manganese oxide is manganese dioxide.

<17> The method for producing α-hydroxyisobutyric acid amide according to any one of items <1> to <16>, wherein the catalyst composed mainly of manganese oxide comprises a compound represented by composition formula: $Mn_aK_bM_cO_d$ wherein: Mn represents manganese; K represents potassium; O represents oxygen; M represents at least one element selected from V, Sn and Bi; and regarding the atomic ratio of each element, when a=1, b is 0.005 to 0.5, c is 0.001 to 0.1, and d is 1.7 to 2.0.

<18> The method for producing α-hydroxyisobutyric acid amide according to item <17>, wherein the catalyst composed mainly of manganese oxide further comprises hydrated water.

<19> The method for producing α-hydroxyisobutyric acid amide according to item <1>, which comprises the step (A) and the step (B).

<20> The method for producing α-hydroxyisobutyric acid amide according to item <19>, wherein the ratio of the amount of acetone cyanohydrin contained in the reaction raw material liquid supplied to the first reaction region to the total amount of acetone cyanohydrin contained in the reaction raw material liquid supplied to the reaction apparatus in the step (A) is 50 to 98% by weight.

<21> The method for producing α-hydroxyisobutyric acid amide according to item <19> or <20>, wherein the circulation ratio in the step (B) is 0.5 to 50 when represented by the volume velocity ratio.

<22> A reaction apparatus for producing α-hydroxyisobutyric acid amide by hydration of acetone cyanohydrin in the presence of a catalyst composed mainly of manganese oxide, wherein the reaction apparatus has at least two reaction regions connected in series and further has:

(a) a piping for supplying a reaction raw material liquid containing acetone cyanohydrin to the first reaction region (I) and at least one reaction region (II) other than the first reaction region in the reaction apparatus; and/or (b) a piping for cyclically supplying at least a portion of a reaction liquid withdrawn from at least one reaction region (III) to the first reaction region (I) in the reaction apparatus.

<23> The reaction apparatus according to item <22>, wherein in (b), the reaction apparatus further has a piping for cyclically supplying at least a portion of the reaction liquid withdrawn from the at least one reaction region (III) to the at least one reaction region (II) other than the first reaction region.

<24> The reaction apparatus according to item <22> or <23>, which further has a piping for supplying a diluent containing at least one compound selected from water, acetone, α-hydroxyisobutyric acid amide and formamide to the at least one reaction region (III).

<25> The reaction apparatus according to any one of items <22> to <24>, which further has a piping for supplying an oxidizing agent to the at least one reaction region (III).

<26> The reaction apparatus according to any one of items <22> to <25>, wherein an equipment for withdrawing the oxidizing agent is connected to the first reaction region (I) and/or a position between the at least one reaction region (II) other than the first reaction region and another reaction region, or the first reaction region (I) and/or the middle portion of the at least one reaction region (II) other than the first reaction region.

EXPLANATIONS OF LETTERS OR NUMERALS

1a: first reactor
1b: second reactor
1c: third reactor
2a: first reaction region
2b: second reaction region
2c: third reaction region
3a, 3b: reaction raw material liquid supply line
4a, 4b, 4c: oxidizing agent supply line
5a, 5b, 5c: oxidizing agent withdrawing line
6a, 6b: circulation line
7: cooler
8: pump
9: heater
10a, 10b, 10c: reaction liquid supply line
11a, 11b, 11c: reaction liquid outflow line
12a, 12b: liquid reservoir
13a, 13b: liquid delivery line

The invention claimed is:

1. A method for producing α-hydroxyisobutyric acid amide by hydration of acetone cyanohydrin in the presence of a catalyst comprising manganese oxide using a reaction apparatus in which two to seven reaction regions are connected in series, wherein the method comprises:

(B) cyclically supplying at least a portion of a reaction liquid withdrawn from at least one reaction region to a first reaction region (I) in the reaction apparatus;

(b1) further cyclically supplying at least a portion of the reaction liquid withdrawn from at least one reaction region to at least one reaction region other than the first reaction region (I), and (C) supplying at least a portion of a reaction liquid withdrawn from at least one reaction region other than the first reaction region (I) to:
i) at least one reaction region other than the first reaction region (I) which is the same as or upstream from the at least one reaction region other than the first reaction region (I) from which the reaction liquid is withdrawn, and
ii) at least one reaction region other than the first reaction region (I) which is downstream from the at least one reaction region other than the first reaction region (I) from which the reaction liquid is withdrawn; wherein
an oxidizing agent is supplied to at least one reaction region in the reaction apparatus, wherein the method further comprises supplying a reaction raw material liquid containing the acetone cyanohydrin to the reaction apparatus, and wherein the concentration of the acetone cyanohydrin in the total amount of the reaction raw material liquid is 30% by weight or more, and
wherein the concentration of manganese eluted from the first reaction region (I) is less than or equal to 4.5 ppm.

2. A method for producing α-hydroxyisobutyric acid amide by hydration of acetone cyanohydrin in the presence of a catalyst comprising manganese oxide using a reaction apparatus in which two to seven reaction regions are connected in series, wherein the method comprises:
(A) supplying a reaction raw material liquid containing the acetone cyanohydrin dividedly to a first reaction region (I) and at least one reaction region other than the first reaction region (I) in the reaction apparatus;
(B) cyclically supplying at least a portion of a reaction liquid withdrawn from at least one reaction region to the first reaction region (I) in the reaction apparatus;
(b1) further cyclically supplying at least a portion of the reaction liquid withdrawn from at least one reaction region to at least one reaction region other than the first reaction region (I), and
(C) supplying at least a portion of a reaction liquid withdrawn from at least one reaction region other than the first reaction region (I) to:
i) at least one reaction region other than the first reaction region (I) which is the same as or upstream from the at least one reaction region other than the first reaction region (I) from which the reaction liquid is withdrawn, and
ii) at least one reaction region other than the first reaction region (I) which is downstream from the at least one reaction region other than the first reaction region (I) from which the reaction liquid is withdrawn; wherein
an oxidizing agent is supplied to at least one reaction region in the reaction apparatus, and wherein the concentration of the acetone cyanohydrin in the total amount of the reaction raw material liquid is 30% by weight or more, and
wherein the concentration of manganese eluted from the first reaction region (I) is less than or equal to 4.5 ppm.

3. The method for producing α-hydroxyisobutyric acid amide according to claim 1, wherein in at least a part of (b1) the reaction liquid withdrawn from the at least one reaction region is cyclically supplied to a reaction region that is downstream from the at least one reaction region.

4. The method for producing α-hydroxyisobutyric acid amide according to claim 3, wherein in at least a part of (b1) the reaction liquid withdrawn from the at least one reaction region is cyclically supplied downstream to the final reaction region in the series of reaction regions.

5. The method for producing α-hydroxyisobutyric acid amide according to claim 1, wherein in (C) the portion of the reaction liquid withdrawn from at least one reaction region other than the first reaction region is cyclically supplied to the same at least one reaction region other than the first reaction region.

6. The method for producing α-hydroxyisobutyric acid amide according to claim 2, wherein the number of the reaction regions to which the reaction raw material liquid containing acetone cyanohydrin is supplied in (A) is 5 or less.

7. The method for producing α-hydroxyisobutyric acid amide according to claim 1, wherein the reaction raw material liquid is supplied to two to seven of the reaction regions of the reaction apparatus and wherein the concentration of the acetone cyanohydrin in the reaction raw material liquid is diluted to 25 wt % or less before being supplied to said two to seven reaction regions using a diluent or a reaction liquid flowing out of or withdrawn from the reaction regions.

8. The method for producing α-hydroxyisobutyric acid amide according to claim 1, wherein an oxygen-containing gas is used as the oxidizing agent, and wherein the oxygen concentration in the oxygen-containing gas is 2 to 50% by volume.

9. The method for producing α-hydroxyisobutyric acid amide according to claim 8, wherein the oxygen-containing gas is supplied to the at least one reaction region in the reaction apparatus while withdrawing a gas having a reduced oxygen concentration from the at least one reaction region in the reaction apparatus.

10. The method for producing α-hydroxyisobutyric acid amide according to claim 1, wherein the catalyst comprising manganese oxide is manganese dioxide.

11. The method for producing α-hydroxyisobutyric acid amide according to claim 1, wherein the catalyst comprising manganese oxide comprises a compound represented by composition formula: $Mn_aK_bM_cO_d$ wherein: Mn represents manganese; K represents potassium; O represents oxygen; M represents at least one element selected from the group consisting of V, Sn, and Bi; and regarding the atomic ratio of each element, a is 1, b is 0.005 to 0.5, c is 0.001 to 0.1, and d is 1.7 to 2.0.

* * * * *